United States Patent
Maurer et al.

(10) Patent No.: US 9,267,213 B1
(45) Date of Patent: Feb. 23, 2016

(54) ELECTROCHEMICAL DEBLOCKING SOLUTION FOR ELECTROCHEMICAL OLIGOMER SYNTHESIS ON AN ELECTRODE ARRAY

(71) Applicant: CustomArray, Inc., Bothell, WA (US)

(72) Inventors: Karl Maurer, Everett, WA (US); John J Cooper, Seattle, WA (US)

(73) Assignee: CustomArray, Inc., Bothwell, WA (US)

( * ) Notice: Subject to any disclaimer, the term of this patent is extended or adjusted under 35 U.S.C. 154(b) by 0 days.

(21) Appl. No.: 14/266,595

(22) Filed: Apr. 30, 2014

Related U.S. Application Data

(63) Continuation of application No. 11/090,096, filed on Mar. 25, 2005, now abandoned.

(51) Int. Cl.

| C07H 21/02 | (2006.01) |
|---|---|
| C07H 21/04 | (2006.01) |
| C07B 41/02 | (2006.01) |
| C07B 41/06 | (2006.01) |
| C25B 3/10 | (2006.01) |

(52) U.S. Cl.
CPC . C25B 3/10 (2013.01); C07B 41/02 (2013.01); C07B 41/06 (2013.01); C07H 21/02 (2013.01); C07H 21/04 (2013.01)

(58) Field of Classification Search
None
See application file for complete search history.

(56) References Cited

U.S. PATENT DOCUMENTS

| 3,950,357 | A | 4/1976 | Kahan et al. |
|---|---|---|---|
| 4,165,320 | A | 8/1979 | Ondetti et al. |
| 4,563,263 | A | 1/1986 | Oyama et al. |
| 4,840,893 | A | 6/1989 | Hill |
| 5,143,854 | A | 9/1992 | Pirrung et al. |
| 5,445,934 | A | 8/1995 | Fodor |
| 5,510,270 | A | 4/1996 | Fodor |
| 5,540,828 | A | 7/1996 | Yacynych |
| 5,653,939 | A | 8/1997 | Hollis et al. |
| 5,667,667 | A | 9/1997 | Southern |
| 5,912,339 | A | 6/1999 | Miller et al. |
| 5,929,208 | A | 7/1999 | Heller et al. |
| 5,953,681 | A | 9/1999 | Cantatore et al. |
| 6,051,380 | A | 4/2000 | Sosnowski |
| 6,093,302 | A | 7/2000 | Montgomery |
| 6,280,595 | B1 | 8/2001 | Montgomery |
| 6,444,111 | B1 | 9/2002 | Montgomery |
| 6,456,942 | B1 | 9/2002 | Anderson |
| 6,475,699 | B2 | 11/2002 | Uetani et al. |
| 6,518,024 | B2 | 2/2003 | Choong et al. |
| 6,576,426 | B2 | 6/2003 | Southern et al. |
| 6,743,564 | B2 | 6/2004 | Hatakeyama et al. |
| 6,780,582 | B1 | 8/2004 | Wagner et al. |
| 6,960,298 | B2 | 11/2005 | Krotz et al. |
| 7,008,769 | B2 | 3/2006 | Henderson et al. |
| 7,541,314 | B2 | 6/2009 | Suciu et al. |
| 2002/0090738 | A1 | 7/2002 | Cozzette |
| 2002/0172963 | A1 | 11/2002 | Kelley |
| 2003/0111356 | A1 | 6/2003 | Strathmann |
| 2003/0113713 | A1 | 6/2003 | Glezer |
| 2003/0134989 | A1 | 7/2003 | Aldrich et al. |
| 2004/0073017 | A1 | 4/2004 | Skrzypcznski |
| 2005/0043894 | A1 | 2/2005 | Fernandez |
| 2005/0212902 | A1 | 9/2005 | Cook |
| 2005/0239112 | A1 | 10/2005 | Padmanabhan |
| 2005/0272088 | A1 | 12/2005 | Cook |
| 2006/0102471 | A1 | 5/2006 | Maurer et al. |
| 2006/0160100 | A1 | 7/2006 | Gao et al. |
| 2006/0231411 | A1 | 10/2006 | Maurer |
| 2007/0065877 | A1 | 3/2007 | Maurer |
| 2007/0072169 | A1 | 3/2007 | Peyvan |
| 2007/0231794 | A1 | 10/2007 | Dill et al. |
| 2007/0292855 | A1 | 12/2007 | Dubin |
| 2008/0035494 | A1 | 2/2008 | Gomez |
| 2008/0039342 | A1 | 2/2008 | Tian |
| 2008/0125327 | A1 | 5/2008 | Kumar |

FOREIGN PATENT DOCUMENTS

| JP | 2005166601 | 6/2006 |
|---|---|---|
| WO | WO9603417 | 2/1996 |
| WO | WO0051721 | 9/2000 |
| WO | WO02090963 | 11/2002 |
| WO | WO03020415 | 3/2003 |

OTHER PUBLICATIONS

Ashfari et al., "Application of Complementary DNA Microarray Technology to Carcinogen Identification, Toxicology, and Drug Safety Evaluation" Cancer Res. 59:4759, (1999).

Bard et al., "Azo, Azoxy and Diazo Compounds," Encyclo. of Electrochemistry of the Elements, 1979, pp. 179-209, vol. XIII-4, NY, NY.

Beier et al., "Versatile Derivatisation of Solid Support Media for Convalent Bonding . . . " Nucleic Acids Research, 1999, pp. 1970-1977, vol. 27, No. 9.

Cahill and Nordhoff, "Protein Arrays & Their Role in Protemics" Adv. Biochem. Engin/Biotechnol., 2003, pp. 177-187, vol. 83.

Campbell et al., "Enzyme-Amplified Amperometric Sandwich Test for RNA and DNA" Anal. Chem., 2002, 158-162, 74(1) American Chemical Society.

Dill et al., "Antigen Detection Using Microelectrode Array Microchips" Analytica Chimica Acta, 2001, pp. 69-78, vol. 444.

Dill et al., "Immunoassays and Sequence-Specific DNA Detection on a Microchip . . . " J. Biochem. Biophys. Methods, 2004, 59 pp. 181-187, Elsevier B.V.

(Continued)

Primary Examiner — Eric Olson
(74) Attorney, Agent, or Firm — Sci-Law Strategies, PC

(57) ABSTRACT

There is disclosed an electrochemical deblocking solution for use on an electrode microarray. There is further disclosed a method for electrochemical synthesis on an electrode array using the electrochemical deblocking solution. The solution and method are for removing acid-labile protecting groups for synthesis of oligonucleotides, peptides, small molecules, or polymers on a microarray of electrodes while substantially improving isolation of deblocking to active electrodes. The method comprises applying a voltage or a current to at least one electrode of an array of electrodes. The array of electrodes is covered by the electrochemical deblocking solution.

20 Claims, 4 Drawing Sheets

(56) References Cited

OTHER PUBLICATIONS

Drummond et al., "Electrochemical DNA Sensors" Nature Biotechnology Oct. 2003, 1192-1199, vol. 21, No. 10 Nature Publishing Group.

Egeland et al., "An Electrochemical Redox Couple Activitated by Microelectrodes for Confined Chemical Patterning of Surfaces" Analytical Chemistry (2002) vol. 74, pp. 1590-1596.

Fledler et al., "Diffusional Electrotitration: Generation of pH Gradients . . . " Analytical Chemistry, Mar. 1. 1995, pp. 820-828, vol. 67, No. 5.

Fodor et al., "Light-Directed, Spatially Addressable Parallel Chemical Synthesis" Science, Feb. 15, 1991, 767-773, vol. 251.

Gao et al., "In Situ Synthesis of Oligonucleotide Microarrays" Biopolymers Mar. 2004, pp. 579-596, vol. 73.

Ghindilis et al., "Immunosensors: Electrochemical Sensing and Other . . . " Biosensors & Bioelectronics 1998, pp. 113-131, vol. 13, No. 1, Elsevier Sciences.

Greene et al., "Protective Groups in Organic Synthesis" Third Edition, Wiley-Interscience, 1999.

Guo, et al., "Direct Fluorescence Analysis of Genetic Polymorphisms by Hybridization with Oligonucleotide . . . " Nucl. Acids Res., 1994, pp. 5456-5465, vol. 22, No. 24.

Hacia "Resequencing and mutational analysis using oligonucleotide microarrays" Nature Genetics 21 Supp.: 42, (1999).

Hacia et al., "Applications of DNA Chips for Genomic Analysis" Mol. Psychiatry, 11/1998, pp. 483-492, vol. 3, No. 6.

Hammerich et al., "Organic Electrochemistry, an Introduction & Guide" ed. by Lund and Baizer, 3rd Edition, 1991 pp. 615-657 Marcel Dekker, Inc., NY.

Johnston, "Gene Chips: Array of Hope for Understanding Gene Regulation" Curr. Biology, Feb. 26, 1998, R171-R174, vol. 8.

Krotz et al., "Large-Scale Synthesis of Antisense Oligonucleotides Without Chlorinated Solvents" Organic Process Res & Dev, 2000, pp. 190-193, vol. 4.

Kurian et al., "DNA Chip Technology" J. Pathology, 1999, pp. 267-271, vol. 187.

Lane et al., "Electrochemistry of Chemisorbed Molecules . . . " J. Physical Chemistry, 1973, pp. 1411-1421, vol. 77, No. 11 ($1^{st}$ Page Only).

Leproust et al., "Characterization of Oligodeoxyribonucleotide Synthesis on Glass Plates" Nucl. Acids Res., 2001, pp. 2171-2180, vol. 29, No. 10.

Lipkowski, et al., "Molecular Adsorption at Metal Electrodes" Electro chimica Acta, 1994, pp. 1045-1056, vol. 39, No. 8/9 (Abstract Only).

Maskos and Southern, "Oligodeoxyribonucleotide Synthesis on Glass Plates", Nucl. Acids Res., 1992, pp. 1679-1684, vol. 20.

Moller et al.. "Anodic oxidation of cyclohexene: Dependence of the product distribution on the reaction variables" Electrochimica Acta, vol. 42, No. 13, Jan. 1, 1997, pp. 1971-1978.

Ono et al., "Nucleosides and Nucleotides. 121. Synthesis of Oligonucleotides . . . " Bioconjugate Chem. 1993, pp. 499-508, vol. 4.

Patolsky et al. "Highly Sensitive Amplified Electronic Detection of DNA . . . " Chem. Eur. J., 2003, pp. 1137-1145, vol. 9, No. 5 Wiley-VCH Weinheim.

Patolsky et al., "Enzyme-Linked Amplified Electrochemical Sensing . . . " Langmuir 1999, vol. 15, No. 1,1 pp. 3703-3706, Am. Chemical Society.

Paul et al., "Acid Binding and Detritylation During Oligonucleotide Synthesis" Nucleic Acids Research, 1196, 3048-3052, vol. 24, No. 15.

Pellois et al., "Peptide Synthesis Based on t-Boc Chemistry & Solution Photogenerated Acids" J. Comb. Chem. 2000, pp. 355-360, vol. 2, No. 4.

Pillai, "Photoremovable Protecting Groups in Organic Chemistry" Synthesis 1980, pp. 1-26, vol. 39.

Ronlan, A. and Parker, V. D., "Anodic oxidation of phenolic compounds. Part II. Products and mechanisms of the anodic oxidation of hindered phenols" J. Chem. Soc. (C), 1971, pp. 3214-3218.

Rossier et al., "Enzyme Linked lmmunsorbent Assay on a Microchip . . . " Lab on a Chip 2001, vol. 1, pp. 153-157, The Royal Society of Chemistry.

Septak, M. "Kinetic Studies on Depurination and Detritylation of CPG-bound Intermediates . . . " Nucleic Acids Research, 1996, pp. 3053-3058, vol. 24, No. 15.

Shchepinov et al., "Steric Factors Influencing Hybridisation of Nucleic Acids to Oligonucleotide Arrays" Nucl., Acids Res., 1997, pp. 115-1161, vol. 25, No. 6.

Shchepinov, M.S., "Oligonucleotide Dendrimers: From Poly-Labeled DNAc617 Probes to Stable Nano-Structures" Glen Report, Dec. 1999, vol. 12, No. 1.

Soriaga et al., "Determination of Orientation of Adsorbed Molecules . . . ", J. Am. Chem. Soc., 1982, pp. 3937-3945, vol. 104.

Stickney et al., "A Survey of Factors Influencing the Stablity of . . . " J. Electroanaly. Chem., 1981, pp. 73-88, vol. 125 (Abstract Only).

Wang, G. et al., "Synthesis of Oligonucleotides Containing . . . " Tetrahedron Letters, 1993, 6721-6724, vol. 34, No. 42, Great Britain.

Wang et al., "Dual Enzyme Electrochemical Coding for Detecting DNA Hybridization" Analyst 2002, 1279-1282, The Royal Society of Chemistry.

Wang, Joseph "Survey and Summary from DNA Biosensors . . . " Nucleic Acids Research 2000, pp. 3011-3016, vol. 28, No. 16 Oxford University Press.

Wilgenbus and Lichter, "DNA Chip Technology Ante Portas" J. Mol. Med., Nov. 1999, pp. 761-768, vol. 77.

Wu and Chen, J. Mater. Chem., 1997, 7(8), pp. 1409-1413.

Xie et al., Amperometric Detection of Nucleic Acid at Femtomolar Levels with a Nucleic Acid/Electrochemical Activator Bilayer on Gold Electrodes, 2004, vol. 76, pp. 1611-1617.

SEQUENCE LISTING

```
<160> NUMBER OF SEQ ID NOS: 1

<210> SEQ ID NO 1
<211> LENGTH: 9
<212> TYPE: DNA
<213> ORGANISM: artificial
<220> FEATURE:
<223> OTHER INFORMATION: microarray probe

<400> SEQUENCE: 1 agctgctat                                                            9
```

ELECTROCHEMICAL DEBLOCKING SOLUTION FOR ELECTROCHEMICAL OLIGOMER SYNTHESIS ON AN ELECTRODE ARRAY

PRIORITY CLAIM

This application claims priority to and is a continuation of U.S. Published Application No. 20007/0034513, entitled "Electrochemical Deblocking Solution for Electrochemical Oligomer Synthesis on an Electrode Array" by Karl Maurer et al. filed Mar. 25, 2005, which is herein expressly incorporated by reference in its entirety.

TECHNICAL FIELD OF THE INVENTION

The present invention relates to an electrochemical deblocking solution and method on an electrode microarray for removing acid-labile protecting groups. The present invention is particularly useful for synthesis of oligonucleotides, peptides, small molecules, branched polymers, or other polymers on an electrode array device having short distances between neighboring electrodes.

BACKGROUND OF THE INVENTION

Rapid developments in the field of DNA microarrays have lead to a number of methods for synthetic preparation of DNA. Such methods include spotting pre-synthesized oligonucleotides, photolithography using mask or maskless techniques, in situ synthesis by printing reagents, and in situ parallel synthesis on a microarray of electrodes using electrochemical deblocking of protective groups. A review of oligonucleotide microarray synthesis is provided by: Gao et al., Biopolymers 2004, 73:579. The synthetic preparation of a peptide array was originally reported in year 1991 using photo-masking techniques. This method was extended in year 2000 to include an addressable masking technique using photogenerated acids and/or in combination with photosensitizers for deblocking. Reviews of peptide microarray synthesis using photolabile deblocking are provided by: Pellois et al., J. Comb. Chem. 2000, 2:355 and Fodor et al., Science, 1991, 251:767. Spotting pre-synthesized peptides or isolated proteins has made peptide arrays. A review of protein or peptide arrays is provided by: Cahill and Nordhoff Adv.

During the synthesis of DNA or peptides on a microarray or other substrate, each successive addition of a respective monomer (i.e., nucleotide or amino acid, respectively) involves the removal of a protecting group to allow addition of the next monomer unit. This process step is often called "deblocking." In such a removal or deblocking step, a specific type of solution can be used that is commonly referred to as a deblocking solution, i.e., the solution deblocks the end of the chain of a DNA, peptide, or other species by removing a protective group to allow the addition of a next monomer unit. In general, protective groups can be acid-labile or base-labile, i.e., acidic conditions remove the acid-labile group and basic conditions remove the base-labile group. Additionally, some protecting groups are labile to only specific types of solvents. Alternatively, deblocking can be accomplished using photo-labile-protecting groups, which can be removed by light of a certain wavelength. A review of photoremoveable protecting chemistry is provided by: Photoremovable Protecting Groups in Organic Chemistry, Pillai, Synthesis 39:1-26 (1980). Use of protective groups is a common technique in organic synthesis. Reviews of protective group chemistry are provided by: Protective Groups in Organic Synthesis, Greene, T. W. and Wuts, P. G. M., Wiley-Interscience, 1999 and Protecting Group Chemistry, Robertson, J., Oxford University Press, 2001.

Protecting groups can be removed by electrochemical methods on an electrode array device as a step in the synthesis of polymers on the microarray (Montgomery, U.S. Pat. Nos. 6,093,302, 6,280,595, and 6,444,111, referred to as the "Montgomery patents" the disclosures of which are incorporated by reference herein). In the Montgomery patents method, protecting groups are removed only at selected electrodes by applying a potential only at the selected electrodes. In order to prevent deprotection at neighboring electrodes, the method and the solution need to confine the electrochemical effects to the region immediately adjacent to the electrode undergoing deblocking. Where an aqueous-based deblock solution having a buffer is used (e.g., the Montgomery patents), the solution likely buffers the generation of acidic or basic species to the region near the electrode and prevents diffusion of such species to adjacent electrodes. However, in organic-based (i.e., non-aqueous) deblock solutions, the mechanism of isolating deblocking is not necessarily well understood but may involve molecular interactions that remove or pacify acidic reagent by some other species.

The Montgomery patents disclose an aqueous-based deblock solution, specifically a 0.10 M solution and a 0.05 M solution of aqueous sodium phosphate buffer. The 0.10 M buffer solution had a pH of 7.2. In addition to the examples using sodium phosphate buffer, the Montgomery patents list various aqueous buffers including acetate buffers, borate buffers, carbonate buffers, citrate buffers, HEPES buffers, MOPS buffers, phosphate buffers, TRIS buffers, and KI solutions.

Southern, U.S. Pat. No. 5,667,667 disclosed an organic deblocking solution consisting of triethylammonium sulfate in acetonitrile (1% v/v sulphuric acid and 3% v/v triethylamine or 0.01% v/v sulphuric acid and 0.03% v/v triethylamine). Stoicheometrically, this organic solution appeared to have excess protons. As shown in the Montgomery patents, the Southern organic solution did not isolate deblocking on the microarray and showed considerable random deblocking around the area away from the active electrodes.

Southern WO/020415 discloses a different method of confinement of an active redox product. Specifically, the active redox product is generated at an active electrode by at least one quenching redox product that is generated at adjacent electrodes. The electrodes are parallel lines of alternating cathodes and anodes. The only deblocking solution disclosed is 25 mM of benzoquinone, 25 mM of hydroquinone, and 25 mM of tetrabutylammonium hexafluorophosphate in acetonitrile. Southern WO/020415 emphasizes that electrolyte is chosen such that the active redox product is quenchable by at least one other redox product. However, Southern WO/020415 fails to address the problem of confinement electrochemically-generated acids in the absence of a quenching redox product.

Hammerich and Svensmark (Anodic Oxidation of Oxygen-Containing Compounds, Hammerich, O., and Svensmark, B. in Organic Electrochemistry, an introduction and guide, edited by Lund, H and Baizer, M. M., Third Edition, Marcel Dekker, Inc., New York, 1991, pp. 615-657) disclose anodic oxidation of a hydroquinone bearing electron-withdrawing substituent under aqueous conditions, in aprotic solvents containing water, or in MeCN in the presence of pyridine. Hammerich and Svensmark further disclosed that dienones undergo acid-catalyzed rearrangement under strongly acidic conditions to reestablish hydroquinone derivatives or quinone if the reagent is water. Thus, Hammerich and Svensmark hydroquinone-benzoquinone redox deblocking system is the same as Southern WO/020415.

Accordingly, there is a need in the art to be able to confine electrochemically-generated reagents for deblocking in an organic deblocking solution. The present invention addresses this issue.

SUMMARY OF THE INVENTION

The present invention provides an electrochemical deblocking solution for use on an electrode microarray. The electrochemical deblocking solution comprises an organic solvent-based solution for the deblocking step in the synthesis of any of a variety of oligomers, including, but not limited to an oligonucleotide, a peptide, oligomer, small molecule, branched polymer, or other polymer, or a combination microarray of small molecules (i.e., combinatorial library). In each case, there is an acid-based chemical "deblocking" step that involves the removal of a blocking moiety on a molecule to allow for covalent binding of a next "mer" in the synthesis of an oligomer. Such a solution will be referred to as a deblocking solution. Electrochemical deblocking is an electrochemical step in a synthesis process, wherein a voltage or a current is applied to any one or more of a number of electrodes on an electrode microarray to locally generate an acid or a base (depending upon whether the electrode is an anode or a cathode) that affects removal of acid- or base-labile protecting groups (moieties) bound to a chemical species.

Preferably, such chemical species is attached to a reaction layer that is, in turn, attached to the electrodes. Such electrodes having applied voltage or current are referred to as active electrodes and are either an anode or a cathode. After deblocking, the chemical species having the protective group removed is exposed to another chemical moiety or monomer (or even a polymer) allowing continued synthesis to enlarge the polymer (oligonucleotide, polypeptide, small molecule, or other polymeric species) at the electrodes where deblocking has occurred.

In one embodiment of the present invention, the electrochemical deblock solution comprises an acid-source reducible solvent, an organic salt, and an organic base. In another embodiment of the present invention, the acid-source reduceable solvent comprises an acid source and a reduceable solvent. In another embodiment of the present invention, the reduceable solvent comprises an organic solvent and a reduceable chemical. In another embodiment of the present invention, the reduceable solvent comprises an organic solvent, an alcohol, and a reduceable chemical.

In one embodiment of the present invention, the electrochemical deblock solution comprises an organic solvent, an alcohol, a benzoquinone derivative, a hydroquinone derivative, an organic salt soluble in the organic solvent, and a organic base. The organic solvent provides a deblocking solution where an aqueous deblock solution cannot be used or is less desirable owing to better performance using an organic based deblocking solution. The organic solvent is any suitable solvent capable of dissolving the components to form the deblocking solution for electrochemical deblocking of acid-labile protecting groups.

Reagents are generated electrochemically and are capable of selectively removing protecting groups from chemical functional groups on an attached molecule. Such reagents are generated at active electrodes by applying a sufficient electrical potential (voltage or current) to the selected electrodes in the presence of the inventive deblocking solution. The deblocking process occurs at the "active" electrodes when an acidic reagent generated by the active electrodes (electrochemically) removes the acid-labile protecting group from the attached molecules.

Sufficient acid production at the active electrode can be generated electrochemically by either setting a voltage potential with reference to ground or by setting the desired amount of current in amperage. Setting the voltage potential ensures that the voltage that is applied is held constant but allows the current to change due to differences in different electrodes at different times. Setting the amperage keeps the current at a constant level by constantly changing the potential in order to meet the amperage goal. Preferably, one sources the current, or keeps the current constant at a desired level by modulating the voltage. Preferably, the current in the deblocking step is from about 1 nA per electrode to about 5 mA per electrode. More preferably, the current is from about 50 nA per electrode to about 2 uA per electrode. Most preferably, the current is about 0.26 uA per electrode (i.e., 260 nA) for electrochemical deblocking.

When voltage control is used, the voltage in the deblocking step is from about 0.1 volts to about 10 volts per active electrode. Preferably, voltage is from about 0.4 volt to about 5 volts per active electrode. More preferably, voltage is from about 0.8 volts to about 2.6 volts per electrode. Most preferably, voltage is approximately 1.3 volts per electrode.

The present invention is exemplified herein by the electrochemical synthesis of molecules containing sequences of amino acids (e.g., peptides or polypeptides or proteins) or nucleic acids but could be readily applied to the synthesis of other oligomers or polymers. Such oligomers or polymers include, but are not limited to, both linear and cyclic polymers of nucleic acids, polysaccharides, and peptides having either alpha-, beta-, or omega-amino acids, polyurethanes, polyesters, polycarbonates, polyureas, polyamides, polyethyleneimines, polyarylene sulfides, polysiloxanes, polyimides, polyacetates, or other polymers. In a preferred embodiment, polypeptides are synthesized on electrode arrays. In another preferred embodiment, oligonucleotides, including DNA, are synthesized on electrode arrays. In another preferred embodiment, the present invention is used for the deblocking step for the synthesis of a microarray of small molecules, including oligonucleotides, polypeptides, branched polymers, and other polymers, wherein the polymer molecules can be different (from each other) at each electrode.

In a preferred embodiment of the present invention, the organic solvent is acetonitrile. In another preferred embodiment of the present invention, the organic solvent is methylene chloride.

Other organic solvents would be acceptable alternatives without departing from the scope of the invention. In general, such other solvents include, but are not limited to, aliphatic hydrocarbons, aromatic hydrocarbons, chlorinated hydrocarbons, alcohols, glycols, glycol ethers, ethers, esters, ketones, aldehydes, amides, and amines.

In a preferred embodiment, the alcohol is methanol, ethanol, propanol, isopropanol, or isobutanol. In the most preferred embodiment, the alcohol is methanol or isopropanol. Other alcohols and glycols are suitable.

In preferred embodiments of the present invention, the electrochemical deblocking solution comprises a concentration of approximately 1 mM to 2 M hydroquinone; approximately 0 mM to 10 mM benzoquinone; approximately 0.1 mM to 200 mM lutidine; and approximately 0.1 to 2 M of organic salt; and the solvent comprises approximately 0% to 60% methanol with the balance acetonitrile.

In one embodiment of the present invention, hydroquinone is replaced by one of the following: thiophenol, 1,4-butanedithiol, 1,3-propanedithiol, or methylthiophene or another suitable thiol. This deblocking solution is used for removal of acid-labile protective groups. The electrochemical deblocking solution comprises approximately 0.1 mM to 2.0 M of thiophenol, 1,4-butanedithiol or 1,3-propanedithiol, methylthiophene, or other thiol, or a combination thereof; approximately 0.1 mM to 1 M of organic salt; approximately 0.1 mM to 200 mM lutidine; and a reducible solvent.

In another embodiment of the present invention, a method of electrochemical deblocking of an acid-labile protecting group is provided and comprises applying a voltage or a current to at least one electrode of an array of electrodes. The array of electrodes is covered by any one of the electrochemical deblocking solutions of the present invention.

In other preferred embodiments of the present invention, the electrochemical deblocking solution comprises concentration of approximately 1 mM to 50 mM 2,5 di(tertbutyl) hydroquinone; approximately 0 mM to 50 mM 2,5 di(tertbutyl) benzoquinone; approximately 0.1 mM to 50 mM diisopropylethylamine; and approximately 0.1 to 2 M of organic salt, wherein the solvent comprises approximately 0% to 50% isopropanol with the balance methylene chloride.

DETAILED DESCRIPTION OF THE INVENTION

Figure 1:
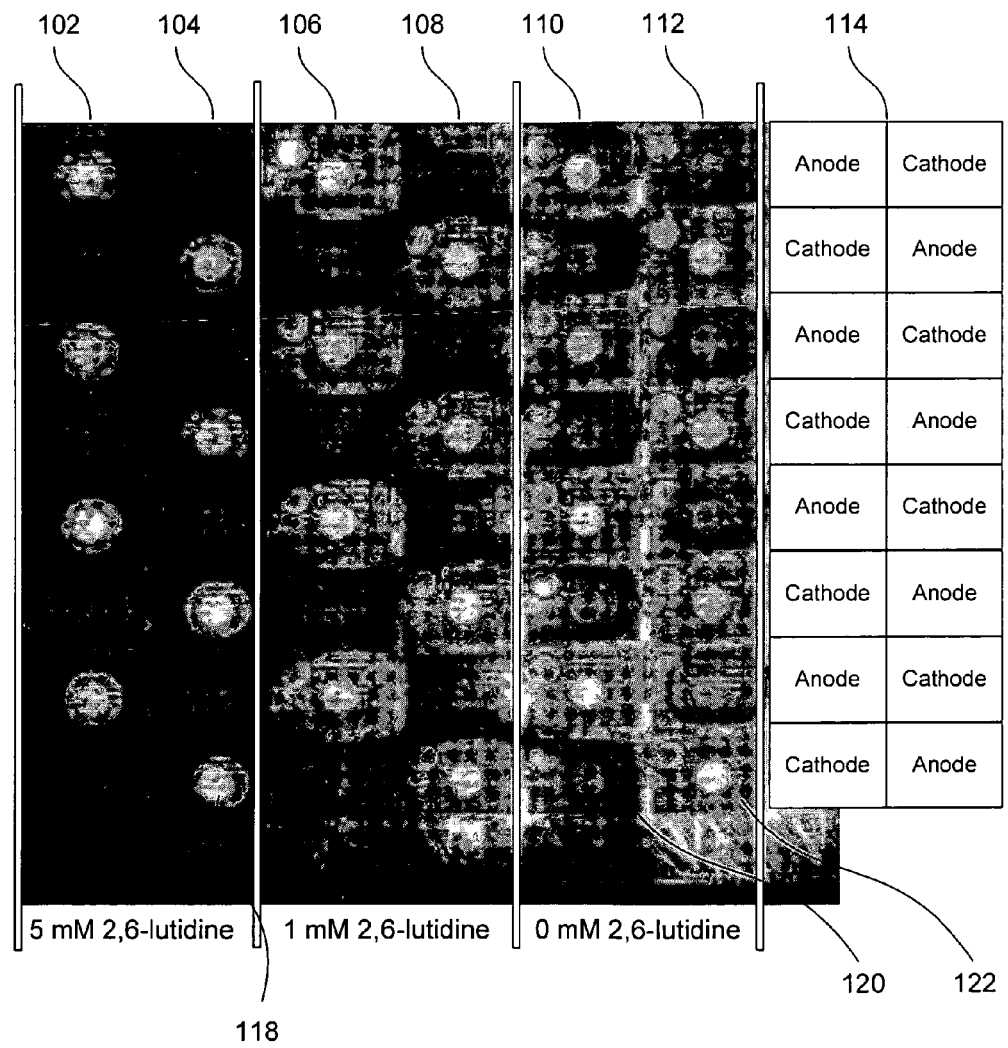
FIG. 1 is a magnified epifluorescence image of a top view of a section of an electrode microarray showing the effect on confinement of acid by 2,6-lutidine in an electrochemical deblocking solution. Lutidine concentration was 0, 1, or 5 mM. Electrochemical deblocking was done at 2 volts for 240 seconds. Cy3 labeled phosphoramidite was coupled to the array to fluorescently image deblocked areas.

As used herein, the term "oligomer" means a molecule of intermediate relative molecular mass, the structure of which essentially comprises a small plurality of units derived, actually or conceptually, from molecules of lower relative molecular mass. A molecule is regarded as having an intermediate relative molecular mass if it has properties which do vary significantly with the removal of one or a few of the units. If a part or the whole of the molecule has an intermediate relative molecular mass and essentially comprises a small plurality of units derived, actually or conceptually, from molecules of lower relative molecular mass, it may be described as oligomeric, or by oligomer used adjectivally. Oligomers are typically comprised of a monomer.

The term "co-oligomer" means an oligomer derived from more than one species of monomer. The term oligomer includes co-oligomers. As examples of oligomers, a single stranded DNA molecule consisting of deoxyadenylate (A), deoxyguanylate (G), deoxycytidylate (C), and deoxythymidylate (T) units in the following sequence, AGCTGCTAT is a co-oligomer, and a single stranded DNA molecule consisting of 10-T units is an oligomer; however, both are referred to as oligomers.

The term "monomer" means a molecule that can undergo polymerization thereby contributing constitutional units to the essential structure of a macromolecule such as an oligomer, co-oligomer, polymer, or co-polymer. Examples of monomers include A, C, G, T, adenylate, guanylate, cytidylate, uridylate, amino acids, vinyl chloride, and other vinyls.

The term "polymer" means a substance composed of macromolecules, which is a molecule of high relative molecular mass, the structure of which essentially comprises the multiple repetition of units derived, actually or conceptually, from molecules of low relative molecular mass. In many cases, especially for synthetic polymers, a molecule can be regarded as having a high relative molecular mass if the addition or removal of one or a few of the units has a negligible effect on the molecular or physical properties. This statement fails in the case of certain macromolecules for which the properties may be critically dependent on fine details of the molecular structure. If a part or the whole of the molecule has a high relative molecular mass and essentially comprises the multiple repetition of units derived, actually or conceptually, from molecules of low relative molecular mass, it may be described as either macromolecular or polymeric, or by polymer used adjectivally.

The term "copolymer" means a polymer derived from more than one species of monomer. Copolymers that are obtained by copolymerization of two monomer species are sometimes termed bipolymers, those obtained from three monomers terpolymers, those obtained from four monomers quaterpolymers, etc. The term polymer includes co-polymers.

Nomenclature for chemical groups mostly follows the recommendations of "The International Union for Pure and Applied Chemistry", Principles of Chemical Nomenclature: a Guide to IUPAC Recommendations, Leigh et al., Science, 1998.

The term "alkyl" means a straight or branched chain alkyl group having a single radical and containing up to approximately 100 but preferably up to 20 carbon atoms. Examples of alkyl groups include but are not limited to the following: methyl, ethyl, n-propyl, isopropyl, n-butyl, isobutyl, sec-butyl, tert-butyl, n-pentyl, isopentyl, neopentyl, tert-pentyl, isohexyl, n-hexyl, n-heptyl, and n-octyl. A substituted alkyl has one or more hydrogen atoms substituted by other groups or one or more carbons replaced by a divalent or trivalent group or atom.

The term "alkenyl" means a straight or branched chain alkyl group having a single radical, having at least one carbon-carbon double bond, and containing up to approximately 100 but preferably up to 20 carbon atoms. Examples of alkenyl groups include but are not limited to the following: vinyl, 1-propenyl, 2-butenyl, 1,3-butadienyl, 2-pentenyl, 2,4-hexadienyl, 4-(ethyl)-1,3-hexadienyl, and 2-(methyl)-3-(propyl)-1,3-butadienyl. A substituted alkenyl has one or more hydrogen atoms substituted by other groups or one or more carbons replaced by a divalent, trivalent, or tetravalent group or atom.

The term "alkynyl" means a straight or branched chain alkyl group having a single radical, having at least one carbon-carbon triple bond, and containing up to approximately 100 but preferably up to 20 carbon atoms. Examples of alkynyl groups include but are not limited to the following: ethynyl, 1-propynyl, 2-propynyl, 1-butynyl, 2-butynyl, 3-butynyl, 4-pentynyl, 5-hexynyl, 6-heptynyl, 7-octynyl, 1-methyl-2-butynyl, 2-methyl-3-pentynyl, 4-ethyl-2-pentynyl, and 5,5-methyl-1,3-hexynyl. A substituted alkynyl has one or more hydrogen atoms substituted by other groups or one or more carbons replaced by a divalent, trivalent, or tetravalent group or atom.

The term "cycloalkyl" means an alkyl group forming at least one ring, wherein the ring has approximately 3 to 14 carbon atoms. Examples of cycloalkyl groups include but are not limited to the following: cyclopropyl, cyclobutyl, cyclopentyl, and cyclohexyl. A substituted cycloalkyl has one or more hydrogen atoms substituted by other groups or one or more carbons replaced by a divalent, trivalent, or tetravalent group or atom.

The term "cycloalkenyl" means an alkenyl group forming at least one ring and having at least one carbon-carbon double bond within the ring, wherein the ring has approximately 3 to 14 carbon atoms. Examples of cycloalkenyl groups include but are not limited to the following: cyclopropenyl, cyclobutenyl, cyclopentenyl, 1,3-cyclopentadienyl, and cyclohexenyl. A substituted cycloalkenyl has one or more hydrogen atoms substituted by other groups or one or more carbons replaced by a divalent, trivalent, or tetravalent group or atom.

The term "cycloalkynyl" means an alkynyl group forming at least one ring and having at least one carbon-carbon triple bond, wherein the ring contains up to approximately 14 carbon atoms. A group forming a ring having at least one triple bond and having at least one double bond is a cycloalkynyl group. An example of a cycloalkynyl group includes but is not limited to cyclooctyne. A substituted cycloalkynyl has one or more hydrogens substituted by other groups or one or more carbons replaced by a divalent, trivalent, or tetravalent group or atom.

The term "aryl" means an aromatic ring group having mostly carbon atoms and a single radical and having approximately 4 to 50 carbon atoms. An aryl ring structure can include a ring with one or two heteroatoms. Examples of aryl groups include but are not limited to the following: phenyl, naphthyl, and anthryl. A substituted aryl has one or more hydrogens substituted by other groups or one or more carbons replaced by a divalent or trivalent group or atom.

The term "hetero," when used in the context of chemical groups, or "heteroatom" means an atom other than carbon or hydrogen. Examples of heteroatoms include but are not limited to the following: oxygen, nitrogen, phosphorous, sulfur, boron, silicon, and selenium.

The term "heterocyclic ring" means a ring structure having at least one ring having at least one heteroatom forming a part of the ring and having approximately 3 to 50 atoms connected to form the ring structure. An example of a heterocyclic ring having 6 atoms is pyridine. Additional examples of heterocyclic ring structures include but are not limited to the following aromatic structures: acridine, carbazole, chromene, imidazole, furan, indole, quinoline, and phosphinoline. Examples of heterocyclic ring structures include but are not limited to the following non-aromatic structures: aziridine, 1,3-dithiolane, 1,3-diazetidine, and 1,4,2-oxazaphospholidine. Examples of heterocyclic ring structures include but are not limited to the following fused aromatic and non-aromatic structures: 2H-furo[3,2-b]pyran, 5H-pyrido[2,3-d]-o-oxazine, 1H-pyrazolo[4,3-d]oxazole, 4H-imidazo[4,5-d]thiazole, selenazolo[5,4-f]benzothiazole, and cyclopenta[b]pyran.

The term "polycyclic" or "polycyclic group" means a carbon ring structure having more than one ring and having approximately 4 to 50 carbons forming the ring structure. Examples of polycyclic groups include but are not limited to the following: bicyclo[1.1.0]butane, bicyclo[5.2.0]nonane, and tricycle[5.3.1.1]dodecane.

The term "halo" or "halogen" means inclusively, fluorine, chlorine, bromine, or iodine.

The term "heteroatom group" means one heteroatom or more than one heteroatoms bound together and having two free valences for forming a covalent bridge between two atoms. For example, the oxy radical, —O— can form a bridge between two methyls to form $CH_3$—O—$CH_3$(dimethyl ether) or can form a bridge between two carbons to form an epoxy such as cis or trans 2,3-epoxybutane,

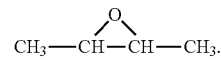

As used herein and in contrast to the normal usage, the term heteroatom group will be used to mean the replacement of groups in an alkyl, alkenyl, alkynyl, cycloalkyl, cycloalkenyl, and cycloalkynyl and not the formation of cyclic bridges, such as an epoxy, unless the term cyclic bridge is used with the term heteroatom group to denote the normal usage Examples of heteroatom groups, using the nomenclature for hetero bridges (such as an epoxy bridge), include but are not limited to the following: azimino (—N═N—HN—), azo (—N═N—), biimino (—NH—NH—), epidioxy (—O—O—), epidithio (—S—S—), epithio (—S—), epithioximino (—S—O—NH—), epoxy (—O—), epoxyimino (—O—NH—), epoxynitrilo (—O—N═), epoxythio (—O—S—), epoxythioxy (—O—S—O—), furano (—$C_4H_2$—), imino (—NH—), and nitrilo (—N═). Examples of heteroatom groups using the nomenclature for forming acyclic bridges include but are not limited to the following: epoxy (—O—), epithio (—S—), episeleno (—Se—), epidioxy (—O—O—), epidithio (—S—S—), lambda$_4$-sulfano (—$SH_2$—), epoxythio (—O—S—), epoxythioxy (—O—S—O—), epoxyimino (—O—NH—), epimino (—NH—), diazano (—NH—NH—), diazeno (—N═N—), triaz[1]eno (—N═N—NH—), phosphano (—PH—), stannano (—$SnH_2$—), epoxymethano (—O—$CH_2$—), epoxyethano —O—CH═CH—CHz— (—O—$CH_2$—$CH_2$—), epoxyprop[1]eno

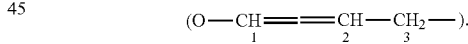

The term "bridge" means a connection between one part of a ring structure to another part of the ring structure by a hydrocarbon bridge. Examples of bridges include but are not limited to the following: methano, ethano, etheno, propano, butano, 2-buteno, and benzeno.

The term "hetero bridge" means a connection between one part of a ring structure to another part of the ring structure by one or more heteroatom groups, or a ring formed by a heterobridge connecting one part of a linear structure to another part of the linear structure, thus forming a ring.

The term "oxy" means the divalent radical —O—.
The term "oxo" means the divalent radical ═O.
The term "carbonyl" means the group

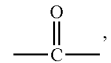

wherein the carbon has two radicals for bonding.

The term "amide" or "acylamino" means the group

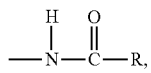

wherein the nitrogen has one single radical for bonding and R is hydrogen or an unsubstituted or substituted alkyl, alkenyl, alkynyl, cycloalkyl, cycloalkenyl, cycloalkynyl, aryl, heterocyclic ring, or polycyclic group.

The term "alkoxy" means the group —O—R—, wherein the oxygen has a single radical and R is hydrogen or an unsubstituted or substituted alkyl, alkenyl, alkynyl, cycloalkyl, cycloalkenyl, cycloalkynyl, aryl, heterocyclic ring, or polycyclic group. Examples of alkoxy groups where the R is an alkyl include but are not limited to the following: methoxy, ethoxy, propoxy, butoxy, pentoxy, hexoxy, heptoxy, octoxy, 1,1-dimethylethoxy, 1,1-dimethylpropoxy, 1,1-dimethylbutoxy, 1,1-dimethylpentoxy, 1-ethyl-1-methylbutoxy, 2,2-dimethylpropoxy, 2,2-dimethylbutoxy, 1-methyl-1-ethylpropoxy, 1,1-diethylpropoxy, 1,1,2-trimethylpropoxy, 1,1,2-trimethylbutoxy, 1,1,2,2-tetramethylpropoxy. Examples of alkoxy groups where the R is an alkenyl group include but are not limited to the following: ethenyloxy, 1-propenyloxy, 2-propenyloxy, 1-butenyloxy, 2-butenyloxy, 3-butenyloxy, 1-methyl-prop-2-enyloxy, 1,1-dimethyl-prop-2-enyloxy, 1,1,2-trimethyl-prop-2-enyloxy, and 1,1-dimethyl-but-2-enyloxy, 2-ethyl-1,3-dimethyl-but-1-enyloxy. Examples of alkyloxy groups where the R is an alkynyl include but are not limited to the following: ethynyloxy, 1-propynyloxy, 2-propynyloxy, 1-butynyloxy, 2-butynyloxy, 3-butynyloxy, 1-methyl-prop-2-ynyloxy, 1,1-dimethyl-prop-2-ynyloxy, and 1,1-dimethyl-but-2-ynyloxy, 3-ethyl-3-methyl-but-1-ynyloxy. Examples of alkoxy groups where the R is an aryl group include but are not limited to the following: phenoxy, 2-naphthyloxy, and 1-anthyloxy.

The term "acyl" means the group

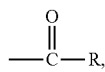

wherein the carbon has a single radical and R is hydrogen or an unsubstituted or substituted alkyl, alkenyl, alkynyl, cycloalkyl, cycloalkenyl, cycloalkynyl, aryl, heterocyclic ring, or polycyclic group. Examples of acyl groups include but are not limited to the following: acetyl, propionyl, butyryl, isobutyryl, valeryl, isovaleryl, acryloyl, propioloyl, mathacryloyl, crotonoyl, isocrotonoyl, benzoyl, and naphthoyl.

The term "acyloxy" means the group

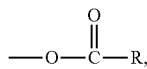

wherein the oxygen has a single radical and R is hydrogen or an unsubstituted or substituted alkyl, alkenyl, alkynyl, cycloalkyl, cycloalkenyl, cycloalkynyl, aryl, heterocyclic ring, or polycyclic group. Examples of acyloxy groups include but are not limited to the following: acetoxy, ethylcarbonyloxy, 2-propenylcarbonyloxy, pentylcarbonyloxy, 1-hexynylcarbonyloxy, benzoyloxy, cyclohexylcarbonyloxy, 2-naphthoyloxy, 3-cyclodecenylcarbonyloxy.

The term "oxycarbonyl" means the group

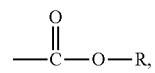

wherein the carbon has a single radical and R is hydrogen or an unsubstituted or substituted alkyl, alkenyl, alkynyl, cycloalkyl, cycloalkenyl, cycloalkynyl, aryl, heterocyclic ring, or polycyclic group. Examples of oxycarbonyl groups include but are not limited methoxycarbonyl, ethoxycarbonyl, isopropyloxycarbonyl, phenoxycarbonyl, and cyclohexyloxycarbonyl.

The term "alkoxycarbonyloxy" means the group

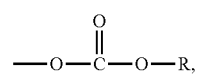

wherein the oxygen has a single radical and R is hydrogen or an unsubstituted or substituted alkyl, alkenyl, alkynyl, cycloalkyl, cycloalkenyl, cycloalkynyl, aryl, heterocyclic ring, or polycyclic group.

The term "carboxy" means the group —C(O)OH, wherein the carbon has a single radical.

The term "amino" means the group —$NH_2$, where the nitrogen has a single radical.

The term "secondary amino" means the group —NH—R, wherein the nitrogen has a single radical and R is hydrogen or an unsubstituted or substituted alkyl, alkenyl, alkynyl, cycloalkyl, cycloalkenyl, cycloalkynyl, aryl, heterocyclic ring, or polycyclic group.

The term "tertiary amino" means the group

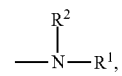

wherein the nitrogen atom has a single radical and $R_1$ and $R_2$ are independently selected from the group consisting of unsubstituted and substituted alkyl, alkenyl, alkynyl, cycloalkyl, cycloalkenyl, cycloalkynyl, aryl, heterocyclic ring, and polycyclic group.

The term "hydrazi" means the group —NH—NH—, wherein the nitrogens have single radicals bound to the same atom. The term "hydrazo" means the group —NH—NH—, wherein the nitrogen atoms have single radicals bound to the different atoms.

The term "hydrazino" means the group $NH_2$—N*H—, wherein the nitrogen (N*) has a single radical.

The term "hydrazono" means the group $NH_2$—N*═, wherein the nitrogen (N*) has two radicals.

The term "hydroxyimino" means the group HO—N*═, wherein the nitrogen (N*) has two radicals.

The term "alkoxyimino" means the group R—O—N*═, wherein the nitrogen (N*) has two radicals and R is an unsubstituted or substituted alkyl, alkenyl, alkynyl, cycloalkyl, cycloalkenyl, cycloalkynyl, aryl, or polycyclic group.

The term "azido" means the group $N_3$—, wherein the nitrogen (N*) has one radical.

The term "azoxy" means the group —N*(O)═N*—, wherein the nitrogens each have one radical.

The term "alkazoxy" means the group R—N(O)=N*—, wherein the nitrogen (N*) has one radical and R is hydrogen or an unsubstituted or substituted alkyl, alkenyl, alkynyl, cycloalkyl, cycloalkenyl, cycloalkynyl, aryl, heterocyclic ring, or polycyclic group. Azoxybenzene is an example compound.

The term "cyano" means the group —CN. The term "isocyano" means the group —NC. The term "cyanato" means the group —OCN. The term "isocyanato" means the group —NCO. The term "fulminato" means the group —ONC. The term "thiocyanato" means the group —SCN. The term "isothiocyanato" means the group —NCS. The term "selenocyanato" means the group —SeCN. The term "isoselenocyanato" means the group —NCSe.

The term "carboxyamido" or "acylamino" means the group

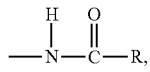

wherein the nitrogen has a single radical and R is hydrogen or an unsubstituted or substituted alkyl, alkenyl, alkynyl, cycloalkyl, cycloalkenyl, cycloalkynyl, aryl, heterocyclic ring, or polycyclic group.

The term "acylimino" means the group

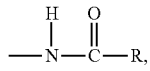

wherein the nitrogen has two radicals and R is hydrogen or an unsubstituted or substituted alkyl, alkenyl, alkynyl, cycloalkyl, cycloalkenyl, cycloalkynyl, aryl, heterocyclic ring, or polycyclic group.

The term "nitroso" means the group O=N—, wherein the nitrogen has a single radical.

The term "aminooxy" means the group —O—NH$_2$, wherein the oxygen has a single radical.

The term "carxoimidioy" means the group

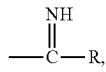

wherein the carbon has a single radical and R is hydrogen or an unsubstituted or substituted alkyl, alkenyl, alkynyl, cycloalkyl, cycloalkenyl, cycloalkynyl, aryl, heterocyclic ring, or polycyclic group.

The term "hydrazonoyl" means the group

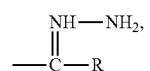

wherein the carbon has a single radical and R is hydrogen or an unsubstituted or substituted alkyl, alkenyl, alkynyl, cycloalkyl, cycloalkenyl, cycloalkynyl, aryl, heterocyclic ring, or polycyclic group.

The term "hydroximoyl" or "oxime" means the group

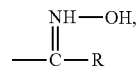

wherein the carbon has a single radical and R is hydrogen or an unsubstituted or substituted alkyl, alkenyl, alkynyl, cycloalkyl, cycloalkenyl, cycloalkynyl, aryl, heterocyclic ring, or polycyclic group.

The term "hydrazino" means the group

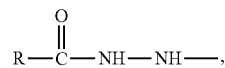

wherein each nitrogen has a single radical and R is hydrogen or an unsubstituted or substituted alkyl, alkenyl, alkynyl, cycloalkyl, cycloalkenyl, cycloalkynyl, aryl, heterocyclic ring, or polycyclic group.

The term "amidino" means the group

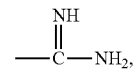

wherein the carbon has a single radical.

The term "sulfide" means the group —S—R—, wherein the sulfur has a single radical and R is hydrogen or an unsubstituted or substituted alkyl, alkenyl, alkynyl, cycloalkyl, cycloalkenyl, cycloalkynyl, aryl, heterocyclic ring, or polycyclic group.

The term "thiol" means the group —S—, wherein the sulfur has two radicals. Hydrothiol means —SH.

The term "thioacyl" means the group —C(S)—R, wherein the carbon has a single radical and R is hydrogen or an unsubstituted or substituted alkyl, alkenyl, alkynyl, cycloalkyl, cycloalkenyl, cycloalkynyl, aryl, heterocyclic ring, or polycyclic group.

The term "sulfoxide" means the group

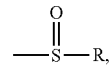

wherein the sulfur has a single radical and R is hydrogen or an unsubstituted or substituted alkyl, alkenyl, alkynyl, cycloalkyl, cycloalkenyl, cycloalkynyl, aryl, heterocyclic ring, or polycyclic group. The term "thiosulfoxide" means the substitution of sulfur for oxygen in sulfoxide; the term includes substitution for an oxygen bound between the sulfur and the R group when the first carbon of the R group has been substituted by an oxy group and when the sulfoxide is bound to a sulfur atom on another group.

The term "sulfone" means the group

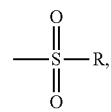

wherein the sulfur has a single radical and R is hydrogen or an unsubstituted or substituted alkyl, alkenyl, alkynyl, cycloalkyl, cycloalkenyl, cycloalkynyl, aryl, heterocyclic ring, or polycyclic group. The term "thiosulfone" means substitution of sulfur for oxygen in one or two locations in sulfone; the term includes substitution for an oxygen bound between the sulfur and the R group when the first carbon of the R group has been substituted by an oxy group and when the sulfone is bound to a sulfur atom on another group.

The term "phosphoric acid ester" means the group $R_1R_22PO_4$—, wherein the oxygen has a single radical and $R_1$ is selected from the group consisting of hydrogen and unsubstituted and substituted alkyl, alkenyl, alkynyl, cycloalkyl, cycloalkenyl, cycloalkynyl, aryl, heterocyclic ring, and polycyclic group, and $R_2$ is selected from the group consisting of unsubstituted and substituted alkyl, alkenyl, alkynyl, cycloalkyl, cycloalkenyl, cycloalkynyl, aryl, heterocyclic ring, and polycyclic group.

The term "substituted" or "substitution," in the context of a chemical species, means independently selected from the group consisting of the replacement of a hydrogen on at least one carbon by a monovalent radical, the replacement of two hydrogens on at least one carbon by a divalent radical, the replacement of three hydrogens on at least one terminal carbon (methyl group) by a trivalent radical, the replacement of at least one carbon and the associated hydrogens (e.g., methylene group) by a divalent, trivalent, or tetravalent radical, and combinations thereof. Meeting valence requirements restricts substitution. Substitution occurs on alkyl, alkenyl, alkynyl, cycloalkyl, cycloalkenyl, cycloalkynyl, aryl, heterocyclic ring, and polycyclic groups, providing substituted alkyl, substituted alkenyl, substituted alkynyl, substituted cycloalkyl, substituted cycloalkenyl, substituted cycloalkynyl, substituted aryl group, substituted heterocyclic ring, and substituted polycyclic groups.

The groups that are substituted on an alkyl, alkenyl, alkynyl, cycloalkyl, cycloalkenyl, cycloalkynyl, aryl, heterocyclic ring, and polycyclic groups are independently selected from the group consisting of alkyl, alkenyl, alkynyl, cycloalkyl, cycloalkenyl, cycloalkynyl, aryl, heterocyclic ring, polycyclic group, halo, heteroatom group, oxy, oxo, carbonyl, amide, alkoxy, acyl, acyloxy, oxycarbonyl, alkoxycarbonyloxy, carboxy, imino, amino, secondary amino, tertiary amino, hydrazi, hydrazino, hydrazono, hydroxyimino, azido, azoxy, alkazoxy, cyano, isocyano, cyanato, isocyanato, thiocyanato, fulminato, isothiocyanato, isoselenocyanato, selenocyanato, carboxyamido, acylimino, nitroso, aminooxy, carboximidoyl, hydrazonoyl, oxime, acylhydrazino, amidino, sulfide, thiol, sulfoxide, thiosulfoxide, sulfone, thiosulfone, thiosulfate, hydroxyl, formyl, hydroxyperoxy, hydroperoxy, peroxy acid, carbamoyl, trimethyl silyl, nitrilo, nitro, aci-nitro, nitroso, semicarbazono, oxamoyl, pentazolyl, seleno, thiooxi, sulfamoyl, sulfenamoyl, sulfeno, sulfinamoyl, sulfino, sulfinyl, sulfo, sulfoamino, sulfonato, sulfonyl, sulfonyldioxy, hydrothiol, tetrazolyl, thiocarbamoyl, thiocarbazono, thiocarbodiazono, thiocarbonohydrazido, thiocarbonyl, thiocarboxy, thiocyanato, thioformyl, thioacyl, thiosemicarbazido, thiosulfino, thiosulfo, thioureido, thioxo, triazano, triazeno, triazinyl, trithio, trithiosulfo, sulfinimidic acid, sulfonimidic acid, sulfinohydrazonic acid, sulfonohydrazonic acid, sulfinohydroximic acid, sulfonohydroximic acid, and phosphoric acid ester, and combinations thereof.

As an example of a substitution, replacement of one hydrogen atom on ethane by a hydroxyl provides ethanol, and replacement of two hydogens by an oxo on the middle carbon of propane provides acetone (dimethyl ketone.) As a further example, replacement the middle carbon (the methenyl group) of propane by the oxy radical (—O—) provides dimethyl ether ($CH_3$—O—$CH_3$.) As a further example, replacement of one hydrogen atom on benzene by a phenyl group provides biphenyl.

As provided above, heteroatom groups can be substituted inside an alkyl, alkenyl, or alkylnyl group for a methylene group (:$CH_2$) thus forming a linear or branched substituted structure rather than a ring or can be substituted for a methylene inside of a cycloalkyl, cycloalkenyl, or cycloalkynyl ring thus forming a heterocyclic ring. As a further example, nitrilo (—N≡) can be substituted on benzene for one of the carbons and associated hydrogen to provide pyridine, or oxy can be substituted to provide pyran.

The term "unsubstituted" means that no hydrogen or carbon has been replaced on an alkyl, alkenyl, alkynyl, cycloalkyl, cycloalkenyl, cycloalkynyl, or aryl group.

The term "lutidine" means isomers of dimethyl pyridine. The isomers include 2,6-, 2,5-, 2,4-, 2,3-, 3,4-, 3,5-, 3,6-, 4,5-, 4,6-, and 5,6-dimethylpyridine.

The term "organic bases" includes organic compounds having nitrogen where the nitrogen provides basicity. Organic bases include nitrogens in substituted and non-substituted ring structures such as pyridine, diethylpyridine, and pyrazole; nitrogens in substituted and non-substituted non-ring structures such as diisopropylethyl amine, triethyl amine, and tributyl amine; and nitrogens in hetero-ring structures or combination ring and non-ring structures with and without substitution. Generally, any amine is included.

The term "acid-source reducible solvent" means a solvent capable of undergoing redox reaction (oxidation) at an anode to provide acidic media adjacent to an activated anode and capable of undergoing redox reaction (reduction) at a cathode to provide current flow in the electrochemical deblocking solution (given sufficient voltage.)

The term "acid source" means a chemical capable of undergoing a redox reaction (oxidation) at an anode to provide an acidic media adjacent to an activated anode.

The term "reducible solvent" means a solvent capable of undergoing redox reaction (reduction) at a cathode to provide current flow in the electrochemical deblocking solution.

The term "reducible chemical" means a chemical in the deblocking solution capable of undergoing redox reaction (reduction) to provide current flow in the electrochemical deblocking solution.

Electrochemical Deblocking Solution

The present invention provides an electrochemical deblocking solution for use on an electrode microarray. The solution is an organic solvent-based solution for the deblocking step in the synthesis of an oligonucleotide, a peptide, oligomer, or other polymer, or a combination microarray of small molecules (i.e., combinatorial library), where removing acid-labile protective groups by electrochemically generated acidic reagent is a step within the synthesis process. Such a solution will be referred to as a deblocking solution. Electrochemical deblocking is an electrochemical step in a synthesis process, wherein a controlled voltage or a controlled current is applied to any one or more of a number of electrodes on an electrode microarray to locally generate an acid or a base (depending upon whether the electrode is an anode or a cathode) that affects removal of acid-labile protecting groups (moieties) bound to a chemical species. Preferably, such chemical species is attached to a reaction layer attached to the electrodes. Such electrodes having applied voltage or current are referred to as active electrodes and are either an anode or a cathode. After deblocking, the chemical species having the protective group removed is exposed to another chemical moiety or monomer (or even a polymer) allowing continued synthesis to enlarge the polymer (oligonucleotide, polypeptide, small molecule, branched polymer, or other polymeric species) at the electrodes where deblocking has occurred.

In one embodiment of the present invention, the electrochemical deblock solution comprises an acid-source reducible solvent, an organic salt, and an organic base. Representative examples of the acid-source reducible solvent include methylene chloride, 1,1,1-trichloroethane, 1,1,2-trichloro-1,2-diifluoroethane, 1,1,2-trichloroethane, 1,4-dichlorobenzene, 1-butanol, 1-hexene, 1-propanol, 2-(2-butoxyethoxy) ethyl acetate, 2-butoxyethanol acetate, 2-butoxyethyl acetate, 2-ethoxyethanol, 2-ethoxyethanol acetate, 2-methoxyethanol acetate, 2-methoxyethanol, 2-methylhexane, 2-nitropropane, acetone alcohol, acetone, acetonitrile, allyl alcohol, benzene, benzotrifluoride, benzyl chloride, biphenyl, carbon disulfide, chlorobenzene, chlorobromomethane, cyclodecane, cycloheptane, cyclohexane, cyclohexanol, cyclohexanone, cyclononane, cyclooctane, cyclopentane, diacetone alcohol, dibromomethane, dichlorodiphenyltrichloroethane, dichloroethene, dimethyl sulfoxide, diethyl ether, diethylene glycol, dimethyl formamide, dipropylene glycol, ethanol, ethyl acetate, ethyl benzene, ethyl ether, ethyl glycol acetate, ethyl glycol, ethylbenzene, ethylene glycol, formamide, furfural, furfuryl alcohol, heptafluorocyclopentane, heptafluoropropyl methyl ether, heptane, hexachlorocyclohexane, hexane, isoamyl alcohol, isobutyl acetate, isobutyl alcohol, isobutyl isobutyrate, isomethoxynonafluorobutane, iso-methoxynonafluorobutane, isophorone, isopropyl acetate, iso-propyl alcohol, methanol, methoxy propyl acetate, methyl amyl ketone, methyl chloride, methyl chloroform, methyl ethyl ketone, methyl glycol acetate methyl isobutyl ketone, methyl propyl ketone, monochlorotoluene, n-amyl alcohol, n-butyl acetate, n-butyl alcohol, n-decane, nitrobenzene, nitromethane, n-methoxynonafluorobutane, n-methylpyrrolidone, n-nonane, n-octane, n-octyl alcohol, n-butyl acetate, n-pentane, n-propyl acetate, n-propyl alcohol, orthodichlorobenzene, perchloroethene, propylene glycol diacetate, propylene glycol, t-amyl alcohol, t-butyl alcohol, tetrahydrofuran, toluene, trans-1,2-dichloroethylene, trichloroethene, trichloroethylene, trichloromethane, triethylene gycol, vinyl choloride, and xylene, and combinations thereof.

The organic salt has a concentration from about 0.1 mM to about 5 M. Representative examples

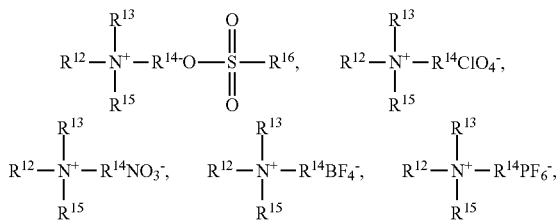

of organic salts include, tetrabutylammonium hexafluorophosphate, tetraethylammonium p-toluenesulfonate, 1,1-dibutyl-pyrrolidinium bis(trifluoromethylsulfonyl)imide, 1,1-dimethyl-pyrrolidinium tris(pentafluoroethyl)trifluorophosphate, 1,1-dipropyl-pyrrolidinium bis(trifluoromethylsulfonyl)imide, 1,2-dimethyl-3-propylimidazolium bis(trifluoromethyl)imide, 1,2-dimethyl-3-propylimidazolium tris(trifluoromethylsulfonyl)methide, 1,3-dimethyl-imidazolium bis(pentafluoroethyl)phosphinate, 1,3-dimethyl-imidazolium methyl sulfate, 1,3-dimethyl-imidazolium trifluoromethanesulfonate, 1-benzyl-3-methyl-imidazolium hexafluoroantimonate, 1-benzyl-3-methyl-imidazolium hexafluorophosphate, 1-benzyl-3-methyl-imidazolium methylsulfate, 1-benzyl-3-methyl-imidazolium tetrafluoroborate, 1-benzyl-3-methyl-imidazolium trifluoromethanesulfonate, -butyl-1-methyl-pyrrolidinium bis(trifluoromethylsulfonyl)imide, 1-butyl-1-methyl-pyrrolidinium dicyanamide, 1-butyl-1-methyl-pyrrolidinium hexafluoroantimonate, 1-butyl-1-methyl-pyrrolidinium hexafluorophosphate, 1-butyl-1-methyl-pyrrolidinium methylsulfate, 1-butyl-1-methyl-pyrrolidinium tetracyanoborate, 1-butyl-1-methyl-pyrrolidinium tetrafluoroborate, 1-butyl-1-methyl-pyrrolidinium trifluoromethanesulfonate, 1-butyl-1-methyl-pyrrolidinium tris(pentafluoroethyl)trifluorophosphate, 1-butyl-2,3-dimethyl-imidazolium hexafluoroantimonate, 1-butyl-2,3-dimethyl-imidazolium hexafluorophosphate, 1-butyl-2,3-dimethyl-imidazolium methylsulfate, 1-butyl-2,3-dimethyl-imidazolium tetrafluoroborate, 1-butyl-2,3-diethyl-imidazolium tosylate, 1-butyl-2,3-dimethyl-imidazolium trifluoromethanesulfonate, 1-butyl-3-ethyl-imidazolium trifluoromethanesulfonate, 1-butyl-3-methyl-imidazolium 2-(2-methoxyethoxy)ethyl sulfate, 1-butyl-3-methyl-imidazolium bis(trifluoromethyl)imide, 1-butyl-3-methyl-imidazolium cobalt tetracarbonyl, 1-butyl-3-methyl-imidazolium dicyanamide, 1-butyl-3-methyl-imidazolium hexafluorophosphate, 1-butyl-3-methyl-imidazolium methyl sulfate, 1-butyl-3-methyl-imidazolium octylsulfate, 1-butyl-3-methyl-imidazolium tetrafluoroborate, 1-butyl-3-methyl-imidazolium tosylate, 1-butyl-3-methyl-imidazolium trifluoroacetate, 1-butyl-3-methyl-imidazolium trifluoromethane sulfonate, 1-butyl-3-methyl-pyridinium bis(trifluormethylsulfonyl)imide, 1-butyl-4-methyl-pyridinium hexafluorophosphate, 1-butyl-4-methyl-pyridinium tetrafluoroborate, 1-butyl-imidazolium hexafluorophosphate, 1-butyl-imidazolium tetrafluoroborate, 1-butyl-imidazolium tosylate, 1-butyl-imidazolium trifluoromethanesulfonate, 1-ethyl-1-methyl-pyrrolidinium bis(trifluoromethyl)imide, 1-ethyl-1-methyl-pyrrolidinium hexafluoroantimonate, 1-ethyl-1-methyl-pyrrolidinium hexafluorophosphate, 1-ethyl-1-methyl-pyrrolidinium methylsulfate, 1-ethyl-1-methyl-pyrrolidinium tetrafluoroborate, 1-ethyl-1-methyl-pyrrolidinium trifluoromethanesulfonate, 1-ethyl-2,3-dimethyl-imidazolium hexaflluoroantimonate, 1-ethyl-2,3-dimethyl-imidazolium hexaflluorophosphate, 1-ethyl-2,3-dimethyl-imidazolium methylsulfate, 1-ethyl-2,3-dimethyl-imidazolium tetrafluoroborate, 1-ethyl-2,3-dimethyl-imidazolium tosylate, 1-ethyl-2,3-dimethyl-imidazolium trifluoromethanesulfonate, 1-ethyl-3-methyl-imidazolium bis(pentafluoroethyl)phosphinate, 1-ethyl-3-methyl-imidazolium bis(pentafluoroethylsulfonyl)imide, 1-ethyl-3-methyl-imidazolium bis(trifluoromethyl)imide, 1-ethyl-3-methyl-imidazolium bis(trifluoromethylsulfonyl)imide, 1-ethyl-3-methyl-imidazolium bis[1,2-benzenediolato(2-)-O,O']-borate, 1-ethyl-3-methyl-imidazolium bis[oxalato(2-)]-borate, 1-ethyl-3-methyl-imidazolium cobalt tetracarbonyl, 1-ethyl-3-methyl-imidazolium dicyanamide, 1-ethyl-3-methyl-imidazolium hexafluoroantimonate, 1-ethyl-3-methyl-imidazolium hexafluorophosphate, 1-ethyl-3-methyl-imidazolium nitrate, 1-ethyl-3-methyl-imidazolium tetrafluoroborate, 1-ethyl-3-methyl-imidazolium tosylate, 1-ethyl-3-methyl-imidazolium trifluoroacetate, 1-ethyl-3-methyl-imidazolium trifluoromethanesulfonate, 1-ethyl-3-methyl-imidazolium trifluoromethyltrifluoroborate, 1-hexyl-1-methyl-pyrrolidinium bis(trifluoromethylsulfonyl)imide, 1-hexyl-1-methyl-pyrrolidinium dicyanamide, 1-hexyl-2,3-dimethyl-imidazolium tetrafluoroborate, 1-hexyl-2,3-dimethyl-imidazolium trifluoromethanesulfonate, 1-hexyl-3-methyl-imidazolium bis(trifluoromethylsulfonyl)imide, 1-hexyl-3-methyl-imidazolium bis(trifluoromethylsulfonyl)methane, 1-hexyl-3-methyl-imidazolium dicyanamide, 1-hexyl-3-methyl-imidazolium hexafluoroantimonate, 1-hexyl-3-methyl-imidazolium hexafluorophosphate, 1-hexyl-3-methyl-imidazolium methylsulfate, 1-hexyl-3-methyl-imidazolium tetracyanoborate, 1-hexyl-3-methyl-imidazolium tetrafluoroborate, 1-hexyl-3-methyl-imidazolium trifluoromethanesulfonate, 1-hexyl-3-methyl-imidazolium tris(heptafluoropropyl)trifluorophosphate, 1-hexyl-3-methyl-imidazolium tris(pentafluoroethyl)trifluorophosphate, 1-hexyl-3-methyl-imidazolium tris(pentafluoroethyl)trifluorophosphate, 1-methyl-3-(3,3,4,4,5,5,6,6,7,7,8,8,8-tridecafluorooctyl)-imidazolium-hexafluorophosphate, 1-methyl-3-octyl-imidazolium tetrafluoroborate, 1-methyl-imidazolium hexafluorophosphate, 1-methyl-imidazolium tetrafluoroborate, 1-methyl-imidazolium tosylate, 1-methyl-imidazolium trifluoromethanesulfonate, 1-octadecyl-3-methyl-imidazolium bis(trifluoromethylsulfonyl)imide, 1-octadecyl-3-methyl-imidazolium hexafluorophosphate, 1-octyl-1-methyl-pyrrolidinium bis(trifluoromethylsulfonyl)imide, 1-octyl-3-methyl-imidazolium bis(trifluoromethylsulfonyl)imide, 1-octyl-3-methyl-imidazolium bis(trifluoromethylsulfonyl)methane, 1-octyl-3-methyl-imidazolium hexafluoroantimonate, 1-octyl-3-methyl-imidazolium hexafluorophosphate, 1-octyl-3-methyl-imidazolium methylsulfate, 1-octyl-3-methyl-imidazolium tetrafluoroborate, 1-octyl-3-methyl-imidazolium trifluoromethanesulfonate, 1-pentyl-3-methyl-imidazolium trifluoromethanesulfonate, 1-pentyl-3-methyl-imidazolium tris(nonafluorobutyl)trifluorophosphate, 1-pentyl-3-methyl-imidazolium tris(pentafluoroethyl)trifluorophosphate, 1-phenylpropyl-3-methyl-imidazolium hexafluoroantimonate, 1-phenylpropyl-3-methyl-imidazolium hexafluorophosphate, 1-phenylpropyl-3-methyl-imidazolium tetrafluoroborate, 1-phenylpropyl-3-methyl-imidazolium trifluoromethanesulfonate, 1-tetradecyl-3-methyl-imidazolium tetrafluoroborate, 3-ethyl-N-butyl-pyridinium hexafluoroantimonate, 3-ethyl-N-butyl-pyridinium hexafluorophosphate, 3-ethyl-N-butyl-pyridinium tetrafluoroborate, 3-ethyl-N-butyl-pyridinium trifluoromethanesulfonate, 3-methyl-1-propyl-pyridinium bis(trifluormethylsulfonyl)imide, 3-methyl-N-butyl-pyridinium hexafluoroantimonate, 3-methyl-N-butyl-pyridinium hexafluorophosphate, 3-methyl-N-butyl-pyridinium methylsulfate, 3-methyl-N-butyl-pyridinium tetrafluoroborate, 3-methyl-N-butyl-pyridinium trifluoromethanesulfonate, 4-methyl-N-butyl-pyridinium hexafluorophosphate, 4-methyl-N-butyl-pyridinium tetrafluoroborate, benzyl triphenylphosphonium bis(trifluoromethyl)imide, bis(trifluoromethylsulfonyl)imide, bis-tetramethyl ammonium oxalate, butyl dimethyl imidazolium hexafluorophosphate, butyl methyl imidazolium hexafluorophosphate, dimethyl distearyl ammonium bisulfate, dimethyl distearyl ammonium methosulfate, ethyl triphenyl phosphonium acetate, guanidinium trifluoromethanesulfonate, guanidinium tris(pentafluoroethyl) Trifluorophosphate, hexamethyl-guanidinium trifluoromethanesulfonate, hexamethyl-guanidinium tris(pentafluoroethyl) trifluorophosphate, methyl trioctyl ammonium bis(trifluoromethylsulfonyl)imide, N,N,N',N',N"-pentamethyl-N"-isopropyl-guanidinium trifluoromethanesulfonate, N,N,N',N',N"-pentamethyl-N"-isopropyl-guanidinium tris(pentafluoroethyl) trifluorophosphate, N,N,N',N',N"-pentamethyl-N"-propyl-guanidinium trifluoromethanesulfonate, N,N,N',N',N"-pentamethyl-N"-propyl-guanidinium tris(pentafluoroethyl) trifluorophosphate, N,N,N',N'-tetramethyl-N"-ethyl-guanidinium trifluoromethanesulfonate, N,N,N',N'-tetramethyl-N"-ethyl-guanidinium tris(pentafluoroethyl) trifluorophosphate, N-butyl-pyridinium bis(trifluoromethyl)imide, N-butyl-pyridinium hexafluoroantimonate, N-butyl-pyridinium hexafluorophosphate, N-butyl-pyridinium methylsulfate, N-butyl-pyridinium tetrafluoroborate, N-butyl-pyridinium trifluoromethanesulfonate, N-hexyl-pyridinium bis(trifluoromethylsulfonyl)imide, N-hexyl-pyridinium bis(trifluoromethylsulfonyl)methane, N-hexyl-pyridinium hexafluorophosphate, N-hexyl-pyridinium tetrafluoroborate, N-hexyl-pyridinium trifluoromethanesulfonate, N-octyl-pyridinium bis(trifluoromethylsulfonyl)imide, N-octyl-pyridinium tris(trifluoromethylsulfonyl)methane, O-ethyl-N,N,N',N'-tetramethyl-isouronium trifluoromethanesulfonate, O-ethyl-N,N,N',N'-tetramethyl-isouronium tris(pentafluoroethyl) trifluorophosphate, O-methyl-N,N,N',N'-tetramethyl-isouronium trifluoromethanesulfonate, O-methyl-N,N,N',N'-tetramethyl-isouronium tris(pentafluoroethyl) trifluorophosphate, S-ethyl-N,N,N',N'-tetramethyl isothiouronium trifluoromethanesulfonate, S-ethyl-N,N,N',N'-tetramethyl-isothiouronium tris(pentafluoroethyl) trifluorophosphate, S-ethyl-N,N,N',N'-tetramethylthiouronium tetrafluoroborate, tetrabutyl ammonium bis(trifluoromethyl)imide, tetrabutyl ammonium bis(trifluoromethylsulfonyl)imide, tetrabutyl ammonium hydrogen sulfate, tetrabutyl ammonium hexafluorophosphate, tetrabutyl ammonium nitrate, tetrabutyl ammonium perchlorate, tetrabutyl ammonium sulfate, tetrabutyl ammonium tetracyanoborate, tetrabutyl ammonium tetrafluoroborate, tetrabutyl ammonium tris(pentafluoroethyl)trifluorophosphate, tetrabutyl phosphonium acetate, tetrabutyl phosphonium bis(trifluoromethyl)imide, tetrabutyl phosphonium bis[1,2-benzenediolato(2-)-O,O']-borate, tetrabutyl phosphonium bis[oxalato(2-)]-borate, tetrabutyl phosphonium tetracyanoborate, tetrabutyl phosphonium tris(pentafluoroethyl)trifluorophosphate, tetraethyl ammonium bis(trifluoromethyl)imide, tetraethyl ammonium bis(trifluoromethylsulfonyl)imide, tetraethyl ammonium bis[1,2-benzenediolato(2-)-O,O']-borate, tetraethyl ammonium bis[2,2'-biphenyldiolato(2-)-O,O']-borate, tetraethyl ammonium bis[malonato(2-)]-borate, tetraethyl ammonium bis[salicylato(2-)]-borate, tetraethyl ammonium hexafluorophosphate, tetraethyl ammonium hydrogen maleate, tetraethyl ammonium tetrafluoroborate, tetraethyl ammonium tosylate, tetraethyl ammonium tris(pentafluoroethyl)trifluorophosphate, tetramethyl ammonium bis(trifluoromethyl)imide, tetramethyl ammonium bis(trifluoromethylsulfonyl)imide, tetramethyl ammonium bis[oxalato(2-)]-borate, tetramethyl ammonium bis[salicylato(2-)]borate, tetramethyl ammonium hexafluorophosphate, tetramethyl ammonium tetrafluoroborate, tetramethyl ammonium tris(pentafluoroethyl)trifluorophosphate, tributylethyl ammonium ethylsulfate, trihexyl(tetradecyl)-phosphonium bis(2,4,4-trimethylpentyl) phosphinate, trihexyl(tetradecyl)-phosphonium bis(trifluoromethylsulfonyl)imide, trihexyl(tetradecyl)-phosphonium bis(trifluoromethylsulfonyl)methane, trihexyl(tetradecyl)-phosphonium bis[1,2-benzenediolato(2-)-O,O']-borate, trihexyl(tetradecyl)-phosphonium decanoate, trihexyl(tetradecyl)-phosphonium dicyanamide, trihexyl(tetradecyl)-phosphonium hexafluorophosphate, trihexyl(tetradecyl)-phosphonium tetracyanoborate, trihexyl(tetradecyl)-phosphonium tetrafluoroborate, trihexyl(tetradecyl)-phosphonium, tris(pentafluoroethyl)trifluorophosphate, and tri-iso-butyl(methyl)-phosphonium tosylate, and combinations thereof. $R^{12}$, $R^{13}$, $R^{14}$, $R^{15}$, and $R^{16}$ are independently selected from the group consisting of substituted and unsubstituted alkyl, alkenyl, alkynyl, cycloalkyl, cycloalkenyl, cycloalkynyl, aryl, heterocyclic ring, and polycyclic group.

The organic base has a concentration of approximately 0.0001 mM to approximately 200 mM. Representative examples of organic bases include N,N-diisopropylethylamine, lutidine(dimethyl pyridine isomers),

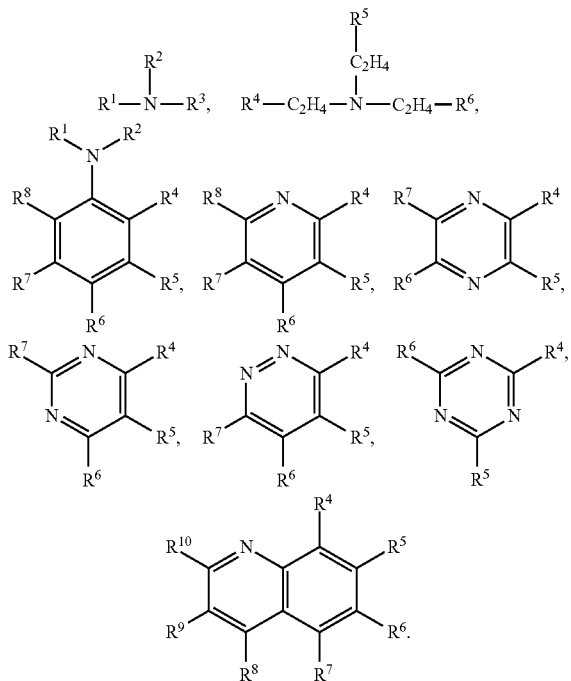

$R^1$, $R^2$, and $R^3$ are independently selected from the group consisting of hydrogen, and substituted and unsubstituted alkyl, alkenyl, alkynyl, cycloalkyl, cycloalkenyl, cycloalkynyl, aryl, heterocyclic ring, and polycyclic group, and halo, amide, carboxy, amino, secondary amino, tertiary amino, hydrazino, azido, alkazoxy, cyano, isocyano, cyanato, thiocyanato, fulminato, selenocyanato, carboxyamido, acylimino, nitroso, aminooxy, hydrazonoyl, oxime, acylhydrazino, amidino, sulfide, thiosulfoxide, sulfone, thiosulfone, thiosulfate, hydroxyl, formyl, hydroperoxy, carbamoyl, trimethyl silyl, nitro, nitroso, oxamoyl, pentazolyl, sulfamoyl, sulfenamoyl, sulfeno, sulfinamoyl, sulfino, sulfo, sulfoamino, hydrothiol, tetrazolyl, thiocarbamoyl, thiocarbazono, thiocarbodiazono, thiocarbonohydrazido, thiocarboxy, thioformyl, thioacyl, thiocyanato, thiosemicarbazido, thiosulfino, thiosulfo, thioureido, triazano, triazeno, triazinyl, trithiosulfo, and phosphoric acid ester.

$R^4$, $R^5$, $R^6$, $R^7$, $R^8$, $R^9$, and $R^{10}$ are independently selected from the group consisting of hydrogen, and substituted and unsubstituted alkyl, alkenyl, alkynyl, cycloalkyl, cycloalkenyl, cycloalkynyl, aryl, heterocyclic ring, and polycyclic group, and halo, amide, alkoxy, acyl, acyloxy, oxycarbonyl, alkoxycarbonyloxy, carboxy, amino, secondary amino, tertiary amino, hydrazino, azido, alkazoxy, cyano, isocyano, cyanato, thiocyanato, fulminato, selenocyanato, carboxyamido, acylimino, nitroso, aminooxy, carboximidoyl, hydrazonoyl, oxime, acylhydrazino, amidino, sulfide, sulfoxide, thiosulfoxide, sulfone, thiosulfone, thiosulfate, hydroxyl, formyl, hydroxyperoxy, hydroperoxy, peroxy acid, carbamoyl, trimethyl silyl, nitro, nitroso, oxamoyl, pentazolyl, sulfamoyl, sulfenamoyl, sulfeno, sulfinamoyl, sulfino, sulfo, sulfoamino, hydrothiol, tetrazolyl, thiocarbamoyl, thiocarbazono, thiocarbodiazono, thiocarbonohydrazido, thiocarboxy, thioformyl, thioacyl, thiocyanato, thiosemicarbazido, thiosulfino, thiosulfo, thioureido, triazano, triazeno, triazinyl, trithiosulfo, and phosphoric acid ester.

In another embodiment of the present invention, the acid-source reducible solvent comprises an acid source and a reducible solvent. The acid source has a concentration of approximately 0.1 mM to approximately 2 M. Representative examples of acid sources include benzophenone, thiophenol, 1,4-butanedithiol, 1,3-propanedithiol, and methylthiophene,

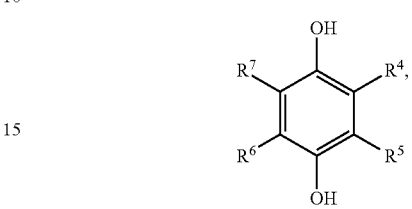

and $R_{17}$—SH, and combinations thereof.

$R^4$, $R^5$, $R^6$, and $R^7$ are independently selected from the group consisting of hydrogen, and substituted and unsubstituted alkyl, alkenyl, alkynyl, cycloalkyl, cycloalkenyl, cycloalkynyl, aryl, heterocyclic ring, and polycyclic group, and halo, amide, alkoxy, acyl, acyloxy, oxycarbonyl, alkoxycarbonyloxy, carboxy, amino, secondary amino, tertiary amino, hydrazino, azido, alkazoxy, cyano, isocyano, cyanato, thiocyanato, fulminato, selenocyanato, carboxyamido, acylimino, nitroso, aminooxy, carboximidoyl, hydrazonoyl, oxime, acylhydrazino, amidino, sulfide, sulfoxide, thiosulfoxide, sulfone, thiosulfone, thiosulfate, hydroxyl, formyl, hydroxyperoxy, hydroperoxy, carbamoyl, trimethyl silyl, nitro, nitroso, oxamoyl, pentazolyl, sulfamoyl, sulfenamoyl, sulfeno, sulfinamoyl, sulfino, sulfo, sulfoamino, hydrothiol, tetrazolyl, thiocarbamoyl, thiocarbazono, thiocarbodiazono, thiocarbonohydrazido, thiocarboxy, thioformyl, thioacyl, thiocyanato, thiosemicarbazido, thiosulfino, thiosulfo, thioureido, triazano, triazeno, triazinyl, trithiosulfo, and phosphoric acid ester.

$R^{17}$ is selected from the group consisting of substituted and unsubstituted alkyl, alkenyl, alkynyl, cycloalkyl, cycloalkenyl, cycloalkynyl, aryl, heterocyclic ring, and polycyclic group, and halo, amide, alkoxy, acyl, acyloxy, oxycarbonyl, alkoxycarbonyloxy, carboxy, amino, secondary amino, tertiary amino, hydrazino, azido, alkazoxy, cyano, isocyano, cyanato, thiocyanato, fulminato, selenocyanato, carboxyamido, acylimino, nitroso, aminooxy, carboximidoyl, hydrazonoyl, oxime, acylhydrazino, amidino, sulfide, sulfoxide, thiosulfoxide, sulfone, thiosulfone, thiosulfate, hydroxyl, formyl, hydroxyperoxy, hydroperoxy, carbamoyl, trimethyl silyl, nitro, nitroso, oxamoyl, pentazolyl, sulfamoyl, sulfenamoyl, sulfeno, sulfinamoyl, sulfino, sulfo, sulfoamino, hydrothiol, tetrazolyl, thiocarbamoyl, thiocarbazono, thiocarbodiazono, thiocarbonohydrazido, thiocarboxy, thioformyl, thioacyl, thiocyanato, thiosemicarbazido, thiosulfino, thiosulfo, thioureido, triazano, triazeno, triazinyl, trithiosulfo, and phosphoric acid ester.

Representative examples of reducible solvents include methylene chloride, 1,1,1-trichloroethane, 1,1,2-trichloro-1,2-diifluoroethane, 1,1,2-trichloroethane, 1,4-dichlorobenzene, 1-butanol, 1-hexene, 1-propanol, 2-(2-butoxyethoxy)ethyl acetate, 2-butoxyethanol acetate, 2-butoxyethyl acetate, 2-ethoxyethanol acetate, 2-ethoxyethanol, 2-methoxyethanol acetate, 2-methoxyethanol, 2-methylhexane, 2-nitropropane, acetone alcohol, acetone, acetonitrile, allyl alcohol, benzene, benzotrifluoride, benzyl chloride, biphenyl, carbon disulfide, chlorobenzene, chlorobromomethane, cyclodecane, cycloheptane, cyclohexane, cyclohexanol, cyclohexanone, cyclononane, cyclooctane, cyclopentane, diacetone alcohol, dibromomethane, dichlorodiphenyltrichloroethane, dichloroethene, dimethyl sulfoxide, diethyl ether, diethylene glycol, dimethyl formamide, dipropylene glycol, ethanol, ethyl acetate, ethyl benzene, ethyl ether, ethyl glycol acetate, ethyl glycol, ethylbenzene, ethylene glycol, formamide, furfural, furfuryl alcohol, heptafluorocyclopentane, heptafluoropropyl methyl ether, heptane, hexachlorocyclohexane, hexane, isoamyl alcohol, isobutyl acetate, isobutyl alcohol, isobutyl isobutyrate, isomethoxynonafluorobutane, iso-methoxynonafluorobutane, isophorone, isopropyl acetate, iso-propyl alcohol, methanol, methoxy propyl acetate, methyl amyl ketone, methyl chloride, methyl chloroform, methyl ethyl ketone, methyl glycol acetate methyl isobutyl ketone, methyl propyl ketone, monochlorotoluene, n-amyl alcohol, n-butyl acetate, n-butyl alcohol, n-decane, nitrobenzene, nitromethane, n-methoxynonafluorobutane, n-methylpyrrolidone, n-nonane, n-octane, n-octyl alcohol, n-butyl acetate, n-pentane, n-propyl acetate, n-propyl alcohol, ortho-dichlorobenzene, perchloroethene, propylene glycol diacetate, propylene glycol, t-amyl alcohol, t-butyl alcohol, tetrahydrofuran, toluene, trans-1,2-dichloroethylene, trichloroethene, trichloroethylene, trichloromethane, triethylene gycol, vinyl choloride, and xylene, and combinations thereof.

In another embodiment of the present invention, the reducible solvent comprises an organic solvent and a reducible chemical. Representative examples of organic solvents include methylene chloride, 1,1,1-trichloroethane, 1,1,2-trichloro-1,2,2-trifluoroethane, 1,1,2-trichloroethane, 1,4-dichlorobenzene, 1-butanol, 1-hexene, 1-propanol, 2-(2-butoxyethoxy) ethyl acetate, 2-butoxyethanol acetate, 2-butoxyethyl acetate, 2-ethoxyethanol acetate, 2-ethoxyethanol, 2-methoxyethanol acetate, 2-methoxyethanol, 2-methylhexane, 2-nitropropane, acetone alcohol, acetone, acetonitrile, allyl alcohol, benzene, benzotrifluoride, benzyl chloride, biphenyl, carbon disulfide, carbon tetrachloride, chlorobenzene, chlorobromomethane, cyclodecane, cycloheptane, cyclohexane, cyclohexanol, cyclohexanone, cyclononane, cyclooctane, cyclopentane, diacetone alcohol, dibromomethane, dichlorodiphenyltrichloroethane, dichloroethene, diemthyl sulfoxide, diethyl ether, diethylene glycol, dimethyl formamide, dipropylene glycol, ethanol, ethyl acetate, ethyl benzene, ethyl ether, ethyl glycol acetate, ethyl glycol, ethylbenzene, ethylene glycol, formamide, furfural, furfuryl alcohol, heptafluorocyclopentane, heptafluoropropyl methyl ether, heptane, hexachlorocyclohexane, hexane, isoamyl alcohol, isobutyl acetate, isobutyl alcohol, isobutyl isobutyrate, isomethoxynonafluorobutane, iso-methoxynonafluorobutane, isophorone, isopropyl acetate, iso-propyl alcohol, methanol, methoxy propyl acetate, methyl amyl ketone, methyl chloride, methyl chloroform, methyl ethyl ketone, methyl glycol acetate methyl isobutyl ketone, methyl propyl ketone, monochlorotoluene, n-amyl alcohol, n-butyl acetate, n-butyl alcohol, n-decane, nitrobenzene, nitromethane, n-methoxynonafluorobutane, n-methylpyrrolidone, n-nonane, n-octane, n-octyl alcohol, n-butyl acetate, n-methoxynonafluorobutane, n-pentane, n-propyl acetate, n-propyl alcohol, ortho-dichlorobenzene, perchloroethene, perchloroethylene, propylene glycol diacetate, propylene glycol, t-amyl alcohol, t-butyl alcohol, tetrachloroethylene, tetrahydrofuran, toluene, trans-1,2-dichloroethylene, trichloroethene, trichloroethylene, trichlorofluoromethane, triethylene gycol, vinyl choloride, and xylene, and combinations thereof.

The reducible chemical has a concentration of approximately 0.001 mM to approximately 200 mM. Representative examples of the reducible chemical include,

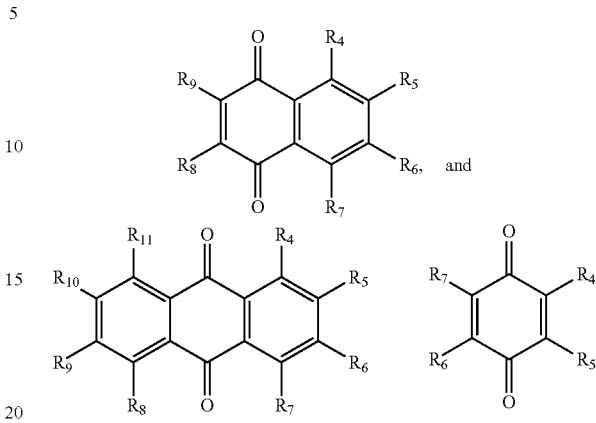

$R^4$, $R^5$, $R^6$, $R^7$, $R^8$, $R^9$, $R^{10}$, and $R^{11}$, are independently selected from the group consisting of hydrogen, and substituted and unsubstituted alkyl, alkenyl, alkynyl, cycloalkyl, cycloalkenyl, cycloalkynyl, aryl, heterocyclic ring, and polycyclic group, and halo, amide, alkoxy, acyl, acyloxy, oxycarbonyl, alkoxycarbonyloxy, carboxy, amino, secondary amino, tertiary amino, hydrazino, azido, alkazoxy, cyano, isocyano, cyanato, thiocyanato, fulminato, selenocyanato, carboxyamido, acylimino, nitroso, carboximidoyl, hydrazonoyl, oxime, acylhydrazino, amidino, sulfide, sulfoxide, thiosulfoxide, sulfone, thiosulfone, thiosulfate, hydroxyl, formyl, hydroxyperoxy, hydroperoxy, carbamoyl, trimethyl silyl, nitro, nitroso, oxamoyl, pentazolyl, sulfamoyl, sulfenamoyl, sulfeno, sulfinamoyl, sulfino, sulfo, hydrothiol, tetrazolyl, thiocarbamoyl, thiocarbazono, thiocarbodiazono, thiocarbonohydrazido, thiocarboxy, thioformyl, thioacyl, thiocyanato, thiosemicarbazido, thiosulfino, thiosulfo, thioureido, triazano, triazeno, triazinyl, trithiosulfo, and phosphoric acid ester.

In another embodiment of the present invention, the reducible solvent comprises an organic solvent, an alcohol, and a reducible chemical. Representative examples of organic solvents include methylene chloride, 1,1,1-trichloroethane, 1,1,2-trichloro-1,2,2-trifluoroethane, 1,1,2-trichloroethane, 1,4-dichlorobenzene, 1-hexene, 2-(2-butoxyethoxy) ethyl acetate, 2-butoxyethanol acetate, 2-butoxyethyl acetate, 2-methoxyethanol acetate, 2-methylhexane, 2-nitropropane, acetone, acetonitrile, benzene, benzotrifluoride, benzyl chloride, biphenyl, carbon disulfide, carbon tetrachloride, chlorobenzene, chlorobromomethane, cyclodecane, cycloheptane, cyclohexane, cyclohexanone, cyclononane, cyclooctane, cyclopentane, dibromomethane, dichlorodiphenyltrichloroethane, dichloroethene, diemthyl sulfoxide, diethyl ether, diethylene glycol, dimethyl formamide, dipropylene glycol, ethyl acetate, ethyl benzene, ethyl ether, ethyl glycol acetate, ethyl glycol, ethylbenzene, ethylene glycol, formamide, furfural, heptafluorocyclopentane, heptafluoropropyl methyl ether, heptane, hexachlorocyclohexane, hexane, isobutyl acetate, isobutyl isobutyrate, isomethoxynonafluorobutane, iso-methoxynonafluorobutane, isophorone, isopropyl acetate, methoxy propyl acetate, methyl amyl ketone, methyl chloride, methyl chloroform, methyl ethyl ketone, methyl glycol acetate methyl isobutyl ketone, methyl propyl ketone, monochlorotoluene, monothiophosphate, n-butyl acetate, n-decane, nitrobenzene, nitromethane, n-methoxynonafluorobutane, n-methylpyrrolidone, n-nonane, n-octane, n-butyl acetate, n-methoxynonafluorobutane, n-pentane, n-propyl acetate, ortho-dichlorobenzene, perchloroethene, perchloroethylene, propylene glycol diacetate, propylene glycol, tetrachloroethylene, tetrahydrofuran, toluene, trans-1,2-dichloroethylene, trichloroethene, trichloroethylene, trichlorofluoromethane, triethylene gycol, vinyl choloride, and xylene, and combinations thereof.

The alcohol is approximately 0% to approximately 90% of the reducible solvent. Representative examples of alcohols include methanol, ethanol, propanol, isobutanol, 1-butanol, 2-ethoxyethanol, 2-methoxyethanol, acetone alcohol, allyl alcohol, cyclohexanol, diacetone alcohol, diethylene glycol, dipropylene glycol, ethyl glycol, ethylene glycol, furfuryl alcohol, isoamyl alcohol, isopropyl alcohol, n-amyl alcohol, n-butyl alcohol, n-octyl alcohol, n-propyl alcohol, propylene glycol, t-amyl alcohol, t-butyl alcohol, and triethylene gycol, and combinations thereof. Representative examples of the reducible chemical are as provided previously.

In one embodiment of the present invention, the electrochemical deblock solution comprises an organic solvent, an alcohol, a benzoquinone derivative, a hydroquinone derivative, an organic salt soluble in the organic solvent, and a reactive organic base. The organic solvent provides a deblocking solution where an aqueous deblock solution cannot be used or is less desirable owing to better performance using an organic based deblocking solution. The organic solvent is any suitable solvent capable of dissolving the components to form the deblocking solution for electrochemical deblocking of acid-labile protecting groups. Without being bound by theory, the amount of alcohol appears to govern the amount of hydroquinone derivative that can be added to the deblock solution; the more alcohol, the more hydroquinone derivative that can be added to the deblock solution. The alcohol may also provide a source of protons at an active electrode. Without being bound by theory, the benzoquinone derivative probably reacts at the cathode to form a hydroquinone derivative or an intermediate. Without being bound by theory, the hydroquinone derivative probably reacts at the anode to form a benzoquinone derivative or an intermediate. Without being bound by theory, the salt provides conductivity to the deblocking solution to allow electrochemical generation of acidic reagent at active electrodes thus causing the deblocking reaction. Without being bound by theory, the reactive organic base confines the electrochemically generated acidic reagent to the active electrode area by reacting with the acidic reagent as it diffuses away from the space immediately above the active electrode.

In the present invention, during a synthesis process on an electrode microarray, a reactive monomer species having an acid-labile protecting group is covalently attached to a reactive layer bound to the electrodes. The protective group prevents a reactive part of the monomer from reacting during synthesis to allow for different structures of polymers (i.e., compilation of monomers) to be synthesized at each electrode, even adjacent electrodes. Alternatively, the monomer species is covalently attached to a preattached chemical species on the prepared surface, such as a linker, which is a short presynthesized (in situ or otherwise) chain of oligonucleotides, peptides, or other polymer species. In either case, subsequent attachment of a monomer species, whether the same species or not, cannot occur without first removing the protecting group from the reactive part of the previously attached monomer by deblocking.

Deblocking is performed by (1) removing any synthesis solution (containing monomers) and introducing the deblock solution into the electrode microarray system to cover the microarray with the deblock solution, (2) addressing the electrodes of the microarray through a computer interface, (3) applying a set voltage or set current to the addressed electrodes to make such electrodes active electrodes thus causing electrochemical reagents to be generated at the electrode surface of only activated electrodes, and (4) removing the deblock solution. By "addressing" selected electrodes it means to apply set voltage or set current to those specific electrodes at a specific site chosen for deblocking to allow the next monomer to be bound. The counter electrode, usually the cathode, to the microarray can be on the microarray itself or can be a separate electrode.

Reagents are generated electrochemically and are capable of selectively removing protecting groups from chemical functional groups on an attached molecule. Such reagents are generated at active electrodes by applying a sufficient electrical potential (voltage or current) to the selected electrodes in the presence of the inventive deblocking solution. The deblocking process occurs at the "active" electrodes when an acidic reagent generated by the active electrodes (electrochemically) removes the acid-labile protecting group from the attached molecules.

Sufficient acid production at the active electrode can be generated electrochemically by either setting a voltage potential with reference to ground or by setting the desired amount of current in amperage. Setting the voltage potential ensures that the voltage that is applied is held constant, but allows the current to change due to differences in different electrodes at different times. Setting the amperage keeps the current at a constant level by constantly changing the potential in order to meet the amperage goal. A most preferred method for most electrochemical deblocking is to source the current, i.e. keep the current constant at a desired level by modulating the voltage. The current in the deblocking step is approximately 1 nA per electrode to approximately 5 mA per electrode. The preferred current is approximately 50 nA per electrode to 2 uA per electrode. A current of 0.26 uA per electrode is currently the preferred current for most electrochemical deblocking in accordance with the present invention. When voltage control is used, the voltage in the deblocking step is approximately 0.1 volts to approximately 10 volts. The preferred voltage is approximately 0.4 volt to approximately 5 volts. A most preferred voltage is approximately 0.8 volts to approximately 2.6 volts. A voltage of approximately 1.3 volts is currently the preferred voltage for most electrochemical deblocking in accordance with the present invention.

The present invention is exemplified with regard to the electrochemical deblocking step in the synthesis on an electrode microarray of molecules containing sequences of amino acids or nucleic acids but could be readily applied to the synthesis of other oligomers or polymers or small molecules. Such oligomers or polymers include, for example, both linear and cyclic polymers of nucleic acids, polysaccharides, and peptides having alpha-, beta-, or omega-amino acids, polyurethanes, polyesters, polycarbonates, polyureas, polyamides, polyethyleneimines, polyarylene sulfides, polysiloxanes, polyimides, polyacetates, branched polymers, or other polymers. In a preferred embodiment, the present invention is used for the deblocking step in the synthesis of polypeptides. In another preferred embodiment, the present invention is used for the deblocking step for the synthesis of oligonucleotides, including DNA. In another preferred embodiment, the present invention is used for the deblocking step for the synthesis of a microarray of small molecules, including oligonucleotides, polypeptides, and other polymers, wherein the polymer molecules can be different (from each other) at each electrode.

The term "protective groups" means materials that bind to a monomer, a linker molecule, or a pre-formed molecule to protect a reactive functionality on the monomer, linker molecule, or pre-formed molecule. Electrochemically generated reagents can remove protective groups. Protective groups that may be used in accordance with the present invention preferably include all acid-labile protecting groups. In another preferred embodiment, hydroxy groups on phosphoramidites are protected by dimethoxytrityl (DMT), which is acid-labile.

Alternatively, other protecting groups can be used and fall within the scope of the present invention. For example, amino groups can be protected by acid-labile protecting groups, such as tert-butyloxycarbonyl, tert-amyloxycarbonyl, adamantyloxycarbonyl, 1-methylcyclobutyloxycarbonyl, 2-(p-biphenyl)propyl(2)oxycarbonyl, 2-(p-phenylazophenylyl)propyl(2)oxycarbonyl, alpha,alpha-dimethyl-3,5-dimethyloxybenzyloxy-carbonyl, 2-phenylpropyl(2)oxycarbonyl, 4-methyloxybenzyloxycarbonyl, benzyloxycarbonyl, furfuryloxycarbonyl, triphenylmethyl (trityl), p-toluenesulfenylaminocarbonyl, dimethylphosphinothioyl, diphenylphosphinothioyl, 2-benzoyl-1-methylvinyl, o-nitrophenylsulfenyl, hexadienyloxycarbonyl, chlorobenzoyloxy, p-methoxy benzyl, methoxy methyl ether, ethoxy methyl ether, tetrahydopyranyl ether, 1-naphthylidene, trimethylsilyl, triethylsilyl, t-butyldimethylsilyl, methoxytrityl, phthaloyl, tert-butyl ester, and dimethyltrityl. As another example, acid-labile groups such as tert-butyl ester can protect carboxylic acid groups.

In a preferred embodiment of the present invention, the organic solvent is acetonitrile. In another preferred embodiment of the present invention, the organic solvent is methylene chloride. Other organic solvents would be acceptable alternatives without departing from the scope of the invention. In general and without being bound by theory, such other solvents may be classified as aliphatic hydrocarbons, aromatic hydrocarbons, chlorinated hydrocarbons, alcohols, glycols, glycol ethers, ethers, esters, ketones, aldehydes, amides, and amines. Solvents of other classes may be suitable and fall within the scope of the present invention.

The following are examples of solvents suitable to practice the present invention: 1,1,1-trichloroethane, 1,1,2-trichloro-1,2,2-trifluoroethane, 1,1,2-trichloroethane, 1,4-dichlorobenzene, 1-butanol, 1-hexene, 1-propanol, 2-(2-butoxyethoxy)ethyl acetate, 2-butoxyethanol acetate, 2-butoxyethyl acetate, 2-ethoxyethanol acetate, 2-ethoxyethanol, 2-methoxyethanol acetate, 2-methoxyethanol, 2-methylhexane, 2-nitropropane, acetic acid, acetone alcohol, acetone, acetonitrile, allyl alcohol, benzene, benzotrifluoride, benzyl chloride, biphenyl, carbon disulfide, carbon tetrachloride, chlorobenzene, chlorobromomethane, cyclodecane, cycloheptane, cyclohexane, cyclohexanol, cyclohexanone, cyclononane, cyclooctane, cyclopentane, diacetone alcohol, dibromomethane, dichlorodiphenyltrichloroethane, dichloroethene, diemthyl sulfoxide, diethanolamine, diethyl ether, diethylene glycol, dimethyl ethanolamine, dimethyl formamide, dipropylene glycol, ethanol, ethyl acetate, ethyl benzene, ethyl ether, ethyl glycol acetate, ethyl glycol, ethylbenzene, ethylene glycol, formamide, formic acid, furfural, furfuryl alcohol, heptafluorocyclopentane, heptafluoropropyl methyl ether, heptane, hexachlorocyclohexane, hexane, isoamyl alcohol, isobutyl acetate, isobutyl alcohol, isobutyl isobutyrate, isomethoxynonafluorobutane, iso-methoxynonafluorobutane, isophorone, isopropyl acetate, iso-propyl alcohol, isopropylamine-striazine, methanol, methoxy propyl acetate, methyl amyl ketone, methyl chloride, methyl chloroform, methyl ethyl ketone, methyl glycol acetate methyl isobutyl ketone, methyl propyl ketone, methylene chloride, monochlorotoluene, monothiophosphate, n-amyl alcohol, n-butyl acetate, n-butyl alcohol, n-decane, nitrobenzene, nitromethane, n-methoxynonafluorobutane, n-methylpyrrolidone, n-nonane, n-octane, n-octyl alcohol, n-butyl acetate, n-methoxynonafluorobutane, n-pentane, n-propyl acetate, n-propyl alcohol, ortho-dichlorobenzene, perchloroethene, perchloroethylene, propylene glycol diacetate, propylene glycol, pyridine, t-amyl alcohol, t-butyl alcohol, tetrachloroethylene, tetrahydrofuran, toluene, trans-1,2-dichloroethylene, trichloroethene, trichloroethylene, trichlorofluoromethane, triethanolamine, triethylene gycol, vinyl choloride, and xylene.

In a preferred embodiment of the present invention, the alcohol is methanol, ethanol, propanol, or isobutanol. In the most preferred embodiment, the alcohol is methanol or isopropanol. Other alcohols and glycols are suitable and fall within the scope of the present invention and include: 1-butanol, 2-butoxyethanol acetate, 2-ethoxyethanol acetate, 2-ethoxyethanol, 2-methoxyethanol acetate, 2-methoxyethanol, acetone alcohol, allyl alcohol, cyclohexanol, diacetone alcohol, diethanol amine, diethylene glycol, dimethyl ethanol amine, dipropylene glycol, ethanol, ethyl glycol acetate, ethyl glycol, ethylene glycol, furfuryl alcohol, isoamyl alcohol, isopropyl alcohol, n-amyl alcohol, n-butyl alcohol, n-octyl alcohol, n-propyl alcohol, propylene glycol diacetate, propylene glycol, t-amyl alcohol, t-butyl alcohol, triethanolamine, and triethylene gycol. The foregoing examples of alcohols and glycols include mixtures of two or more alcohols or glycols provided that the alcohol or glycol is soluble in the solvent to form the deblocking solution of the present invention, wherein removal of acid-labile protecting groups is accomplished in an electrochemical deblocking step.

In preferred embodiments of the present invention, the electrochemical deblocking solution has a concentration of approximately 1 mM to 2 M hydroquinone; approximately 0 mM to 20 mM benzoquinone; approximately 0.0001 mM to 200 mM lutidine; and approximately 0.1 to 5 M of organic salt; and the solvent comprises approximately 0% to 80% methanol with the balance acetonitrile.

In one embodiment of the present invention, hydroquinone and benzoquinone are replaced by thiophenol, 1,4-butanedithiol, 1,3-propanedithiol, methylthiophene or another thiol. This deblocking solution is used for removal of acid-labile protective groups. The electrochemical deblocking solution comprises approximately 0.1 mM to 2.0 M of thiophenol, 1,4-butanedithiol, 1,3-propanedithiol, methylthiophene, or other thiol, or a combination thereof; approximately 0.1 mM to 5 M of organic salt; approximately 0.0001 mM to 200 mM lutidine; and a reducible solvent.

In another embodiment of the present invention, hydroquinone and benzoquinone are replaced by thiophenol, 1,4-butanedithiol, 1,3-propanedithiol, methylthiophene, or another thiol. This deblocking solution is used for removal of acid-labile protective groups. The electrochemical deblocking solution comprises approximately 0.1 mM to 2.0 M of thiophenol, 1,4-butanedithiol or 1,3-propanedithiol, or methylthiophene, or a combination thereof; approximately 0.0001 mM to 200 mM lutidine; and approximately 0.1 to 5 M of organic salt; and the solvent comprises approximately 0% to 60% methanol with the balance acetonitrile.

In another embodiment of the present invention, a method of electrochemical deblocking of an acid-labile protecting group is provided and comprises applying a set voltage or a set current to at least one electrode of an array electrodes. The array of electrodes is covered by any one of the electrochemical deblocking solutions of the present invention.

The following examples are provided merely to explain, illustrate, and clarify the present invention and not to limit the scope of the present invention.

EXAMPLE 1

One preferred deblocking solution comprises 1 M hyrdroquinone, 10 mM benzoquinone, 50 mM tetraethyl ammonium p-toluene sulfonate, 5 mM 2,6-lutidine, 20% methanol, 80% acetonitrile. The solution is made by first mixing the methanol and acetonitrile. After adding all components, approximately one liter of solution was obtained because there was a significant increase in volume owing to the amount of hydroquinone in solution. Benzoquinone was added first, then hydroquinone, then the salt, and then lutidine. The benzoquinone was added first because it will not dissolve adequately if not added first. The solution was mixed using a stir bar on a stir plate. Mixing was performed until all components were dissolved. Mixing continued until the solution was required to be used.

EXAMPLE 2

Electrochemical deblocking solutions were made in accordance with the present invention to test the effectiveness of organic base for confinement of deblocking to the anodes. The procedure comprised using the coupling of Cy3 (fluorescent) phosphoramidite to detect the efficiency and quality of dimethoxytrityl (DMT) removal by acid generated electrochemically in the presence of an electrochemical deblocking solution containing selected amounts of lutidine. Specifically, electrode microarray chips were initialized with a 5-mer oligonucleotide containing a DMT blocked 5' hydroxyl group. Acid was generated electrochemically over specific electrodes to remove the DMT blocking group in the presence of varying amounts of lutidine. A Cy3 phosphoramidite was coupled to any non-DMT-blocked 5' hydroxyls allowing one to visualize electrochemical deblocking using a fluorescent microscope.

The same oligonucleotide was synthesized at each electrode (ACTGT, 5'.fwdarw.3'). The DMT was left on the final "A" nucleotide base for testing the effect of organic base on electrochemical deblocking. Electrochemical deblocking solutions were made comprising 50 nM hydroquinone, 2.5 mM anthraquinone, 50 mM tetraethyl ammonium p-toluene sulfonate, and varying amounts of 2,6-lutidine as the organic base in a solvent comprising 10% methanol and 90% acetonitrile by volume. Lutidine concentrations were 0, 1, or 5 mM. Electrochemical deblocking was done using a constant voltage of 2.0 volts for 240 seconds. After deblocking Cy3 phosphoramidite coupling was performed to view the deblocked areas.

Referring to FIG. 1, the top view of an electrode array is shown magnified. The pattern shows alternating anodes and cathodes in a two-column format 114 for each concentration of lutidine 0 mM (110, 112), 1 mM (106, 108), and 5 mM (102, 104). When lutidine was present in the deblocking solution at 5 mM 102, 104 or 1 mM 106, 108, deblocking was more confined to the region near the anodes as seen by a decrease the light area outside the immediate region of the anodes 118. The anodes had poor confinement without lutidine 122 as seen by the spread of the light area owing to Cy3 fluorescence.

EXAMPLE 3

Electrochemical deblocking solutions were made in accordance with the present invention to test the effectiveness of organic base for confinement of deblocking to the anodes. The procedure comprised using the coupling of Cy3 phosphoramidite to detect the efficiency and quality of dimethoxytrityl (DMT) removal by acid generated electrochemically with electrochemical deblocking solution containing selected amounts of lutidine. Specifically, electrode microarray chips were initialized with a 5-mer oligomer containing a DMT blocked 5' hydroxyl. Acid was generated electrochemically over specific electrodes to remove the DMT in the presence of varying amounts of lutidine. A Cy3 phosphoramidite was coupled to any non-DMT-blocked 5' hydroxyls allowing one to visualize electrochemical deblocking using a fluorescent microscope.

The same oligonucleotide was synthesized at each electrode (ACTGT, 5'.fwdarw.3'). The DMT blocking group was left on the final "A" nucleotide base for testing the effect of organic base on electrochemical deblocking. Electrochemical deblocking solutions were made comprising 50 nM hydroquinone, 2.5 mM anthraquinone, 50 mM tetraethyl ammonium p-toluene sulfonate, and varying amounts of 2,6-lutidine as the organic base in a solvent comprising 10% methanol and 90% acetonitrile by volume. Lutidine concentrations were 0, 5, or 25 mM. Electrochemical deblocking was done using a constant voltage of 2.0 volts for 60 seconds. After deblocking Cy3 phosphoramidite coupling was performed to view the deblocked areas.

Figure 2:
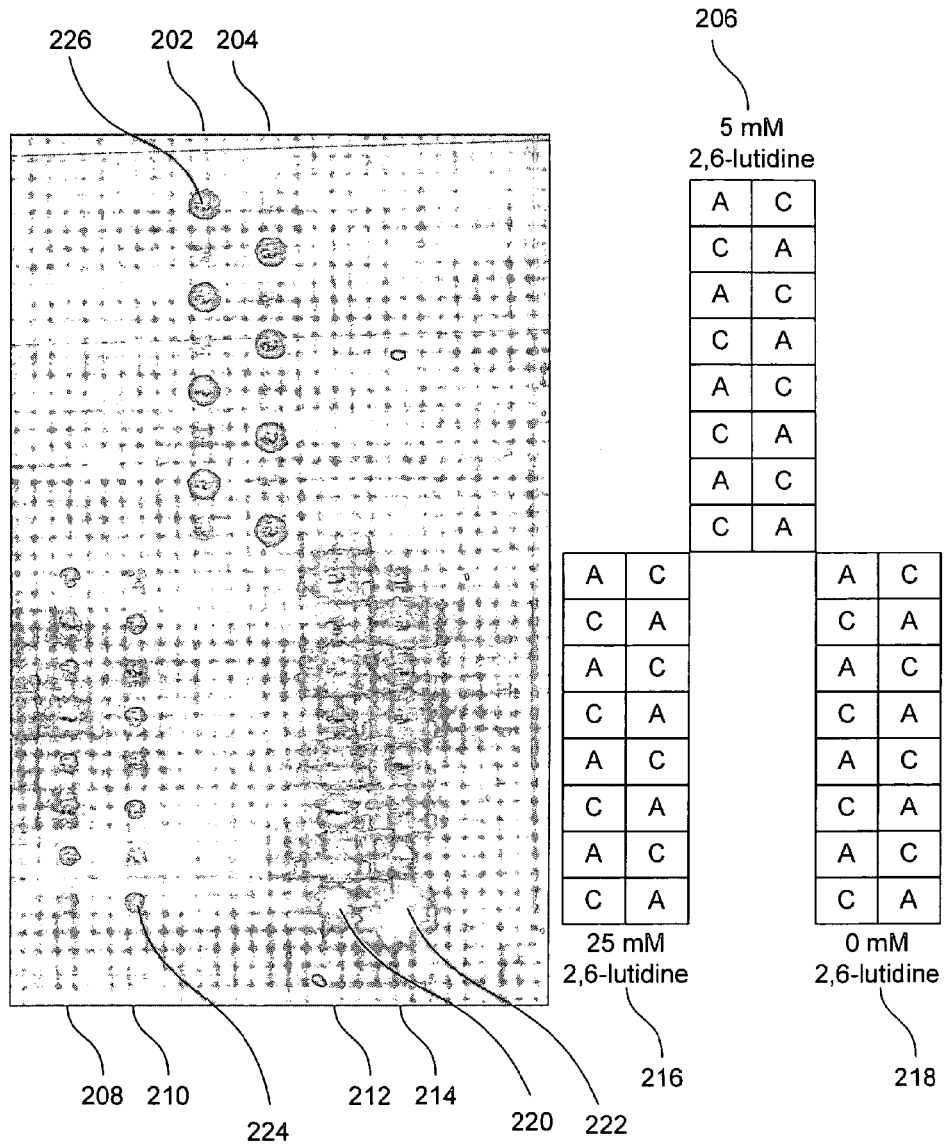
FIG. 2 is a magnified epifluorescence image of a top view of a section of an electrode microarray showing the effect on confinement of acid by 2,6-lutidine in an electrochemical deblocking solution. Lutidine concentration was 0, 5, or 25 mM. Electrochemical deblocking was done at 2 volts for 60 seconds. Cy3 labeled phosphoramidite was coupled to the array to fluorescently image deblocked areas.

Referring to FIG. 2, the top view of an electrode array is shown magnified. The pattern shows alternating anodes and cathodes in a two-column format 218, 206, 216 for each concentration of lutidine 0 mM (212, 214), 5 mM (202, 204), and 25 mM (208, 210). When lutidine was present in the solution at 25 mM 208, 210 or 5 mM 202, 204, deblocking was more confined to the region near the anodes, as seen by a decrease the light area outside the immediate region of the anodes 224, 226. The anodes had poor confinement without lutidine 222 as seen by the spread of the light area owing to Cy3 fluorescence.

EXAMPLE 4

In this assay, a 35-mer DNA oligonucleotide was synthesized on an electrode microarray, wherein each electrode had a different sequence. After synthesis, the oligonucleotides were chemically deprotected. The area of synthesis (and hence electrochemical deblocking during synthesis) was determined by hybridizing a random 9-mer DNA oligomer having a Cy5 label on the 5' end at a concentration of 1 nM in 6.times.SSPE+0.1% Tween for 1 hour at four degrees Celsius. The microarray was washed three times using 6.times.SSPE and then imaged in 6.times.SSPE on an Axon GenePix.RTM. scanner for Cy5 fluorescence.

Figure 3:
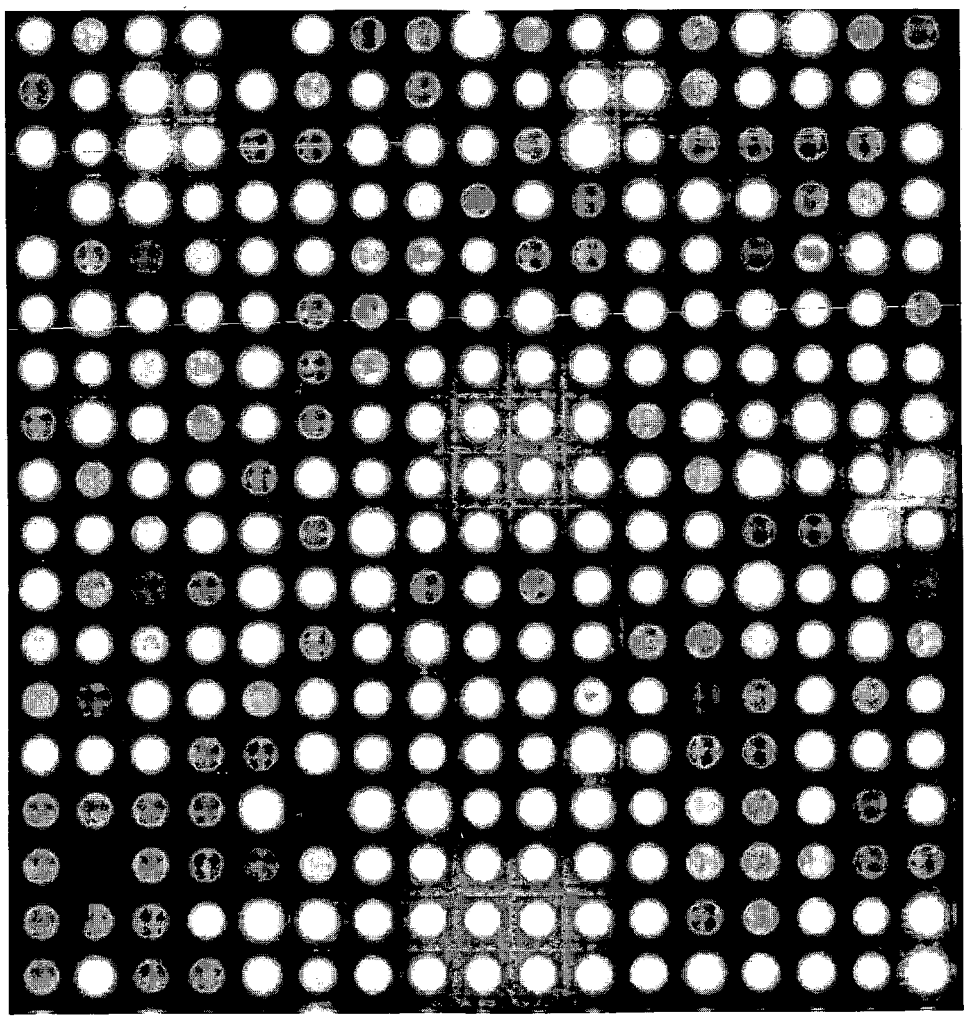
FIG. 3 is a magnified epifluorescence image of a top view of a section of an electrode microarray showing the effect of not having an organic base in the deblock solution as evidenced by the white haze surrounding some of the anodes. Cy3 labeled phosphoramidite was coupled to the array to fluorescently image deblocked areas.
Figure 4:
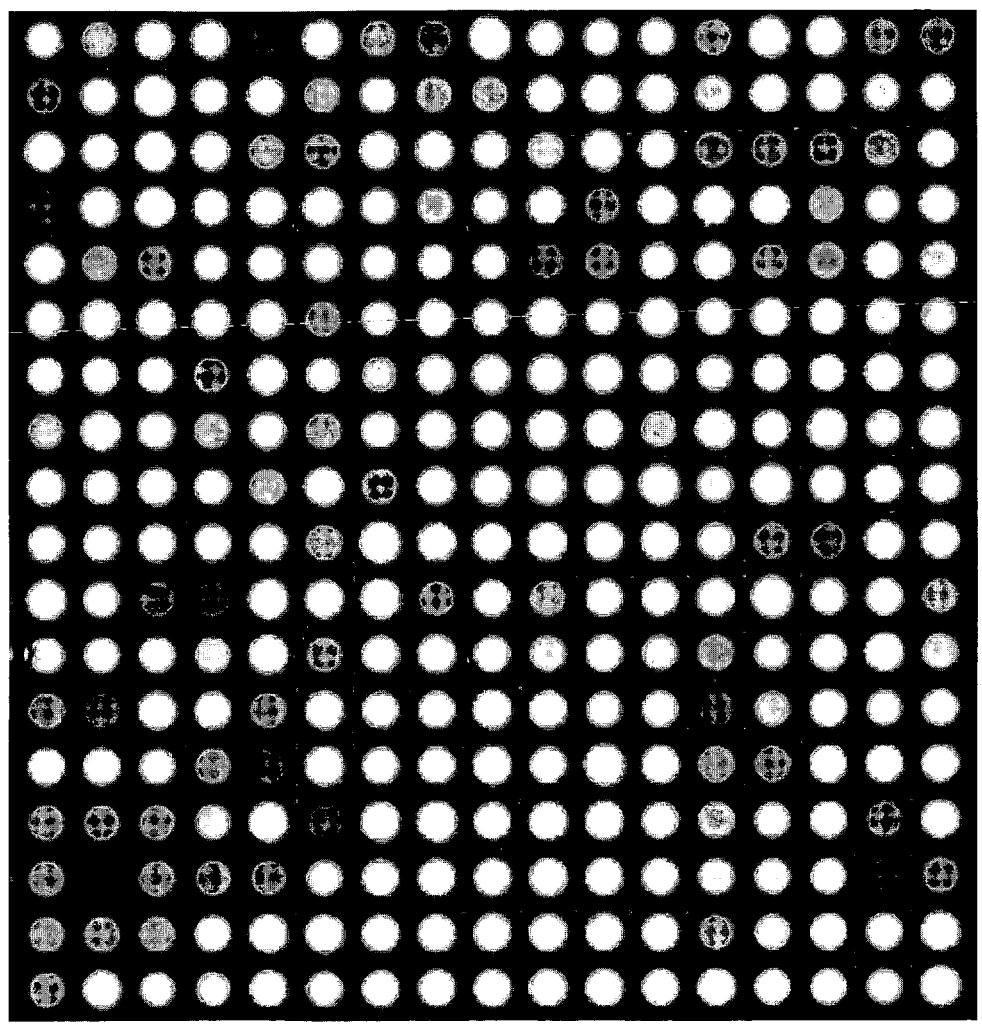
FIG. 4 is a magnified epifluorescence image of a top view of a section of an electrode microarray showing the effect of having an organic base in the deblock solution as evidenced by the lack of a white haze. Cy3 labeled phosphoramidite was coupled to the array to fluorescently image deblocked areas.

Electrochemical deblocking solutions were made comprising 1 M hydroquinone, 10 mM benzoquinone, 50 mM tetraethyl ammonium p-toluene sulfonate, and varying amounts of 2,6-lutidine as the organic base in a solvent comprising 20% methanol and 80% acetonitrile by volume. Lutidine concentration was 0 or 5 mM. In FIG. 3, electrochemical deblocking was done using no lutidine and 0.125 microamperes per electrode for 60 seconds. In FIG. 4, electrochemical deblocking was done using 5 mM lutidine and 0.26 microamperes per electrode for 60 seconds. In FIG. 3, the halo of white in surrounding some of the electrodes indicates deblocking in those areas away from the electrodes. In FIG. 4 where lutidine in present in solution, the halo of white is missing, which indicates lack of deblocking away from the electrodes.

EXAMPLE 5

Electrochemical deblocking solutions have been made using the following formulations shown in Table 1.

TABLE 1

Formulations of electrochemical deblocking solutions.

| Formulation # | Item | Amount |
|---|---|---|
| 1 | Methylene chloride | 180 ml |
| | Isopropyl alcohol | 20 ml |
| | tetrabutylammonium hexafluorophosphate | 3.8 g |
| | 2,5-di-t-butyl hydroquinone | 0.82 g |
| | 2,5-di-t-butyl benzoquinone | 0.82 g |
| | 2,6-lutidine | 233 uL |
| 2 | Methylene chloride | 180 ml |
| | Isopropyl alcohol | 20 ml |
| | tetrabutylammonium hexafluorophosphate | 3.8 g |
| | 2,5-di-t-butyl hydroquinone | 0.82 g |
| | 2,5-di-t-butyl benzoquinone | 0.82 g |
| | Tetraethylammonium acetate | 10 mM |
| 3 | Methylene chloride | 180 ml |
| | Isopropyl alcohol | 20 ml |
| | tetrabutylammonium hexafluorophosphate | 3.8 g |
| | 2,5-di-t-butyl hydroquinone | 0.82 g |
| | 2,5-di-t-butyl benzoquinone | 0.82 g |
| | Tetrabutylammonium hydroxide | 10 mM |
| 4 | Methylene chloride | 180 ml |
| | Isopropyl alcohol | 20 ml |
| | tetrabutylammonium hexafluorophosphate | 3.8 g |
| | 2,5-di-t-butyl hydroquinone | 0.82 g |
| | 2,5-di-t-butyl benzoquinone | 0.82 g |
| | Tetrabutylammonium trichloroacetate | 10 mM |
| 5 | Methylene chloride | 180 ml |
| | Isopropyl alcohol | 20 ml |
| | tetrabutylammonium hexafluorophosphate | 3.8 g |
| | 2,5-di-t-butyl hydroquinone | 0.82 g |
| | 2,5-di-t-butyl benzoquinone | 0.82 g |
| | Tetrabutylammonium acetate | 10 mM |
| 6 | Methylene chloride | 180 ml |
| | Isopropyl alcohol | 20 ml |
| | tetrabutylammonium hexafluorophosphate | 3.8 g |
| | 2,5-di-t-butyl hydroquinone | 0.82 g |
| | 2,5-di-t-butyl benzoquinone | 0.82 g |
| | Tetrabutylammonium dichloroacetate | 10 mM |
| 7 | Methylene chloride | 180 ml |
| | Isopropyl alcohol | 20 ml |
| | tetrabutylammonium hexafluorophosphate | 3.8 g |
| | 2,5-di-t-butyl hydroquinone | 0.82 g |
| | 2,5-di-t-butyl benzoquinone | 0.82 g |
| | N,N-diisopropyl ethylamine | 2.5 mM |
| 8 | Methylene chloride | 180 ml |
| | Isopropyl alcohol | 20 ml |
| | tetrabutylammonium hexafluorophosphate | 3.8 g |
| | 2,5-di-t-butyl hydroquinone | 0.82 g |
| | 2,5-di-t-butyl benzoquinone | 0.82 g |
| | N,N-diisopropyl ethylamine | 5 mM |
| 9 | Methylene chloride | 180 ml |
| | Isopropyl alcohol | 20 ml |
| | tetrabutylammonium hexafluorophosphate | 3.8 g |
| | 2,5-di-t-butyl hydroquinone | 0.82 g |
| | 2,5-di-t-butyl benzoquinone | 0.82 g |
| | N,N-diisopropyl ethylamine | 10 mM |
| 10 | Methylene chloride | 180 ml |
| | Isopropyl alcohol | 20 ml |
| | tetrabutylammonium hexafluorophosphate | 3.8 g |
| | 2,5-di-t-butyl hydroquinone | 0.82 g |
| | 2,5-di-t-butyl benzoquinone | 0.82 g |
| | N,N-diisopropyl ethylamine | 20 mM |
| 11 | Methylene chloride | 180 ml |
| | Isopropyl alcohol | 20 ml |
| | tetrabutylammonium hexafluorophosphate | 3.8 g |
| | 2,5-di-t-butyl hydroquinone | 0.82 g |
| | 2,5-di-t-butyl benzoquinone | 0.82 g |
| | tertbutylammonium dihydrogen phosphate | 10 mM |

EXAMPLE 6

Electrochemical deblocking solutions are made using the following formulations shown in Table 2.

TABLE 2

Formulations of electrochemical deblocking solutions.

| Solvent | Alcohol | Acid Source | Reducible Chemical | Organic Salt | Organic Base |
|---|---|---|---|---|---|
| Acetonitrile (%) | Methanol (%) | Hydroquinone (mM) | Benzoquinone (mM) | Tetraethyl ammonium p-toluene sulfonate (mM) | Lutidine (mM) |
| 100 | 0 | 750 | 10 | 50 | 5 |
| 80 | 20 | 1000 | 10 | 50 | 5 |
| 60 | 40 | 1000 | 10 | 50 | 5 |
| 40 | 60 | 1000 | 10 | 50 | 5 |
| 20 | 80 | 1000 | 10 | 50 | 5 |
| 0 | 100 | 1000 | 10 | 50 | 5 |
| 80 | 20 | 0.1 | 10 | 50 | 5 |
| 80 | 20 | 50 | 10 | 50 | 5 |
| 80 | 20 | 200 | 10 | 50 | 5 |
| 80 | 20 | 1000 | 10 | 50 | 5 |
| 80 | 20 | 2,000 | 10 | 50 | 5 |
| 60 | 40 | 2,000 | 10 | 50 | 5 |
| 80 | 20 | 1000 | 0.1 | 50 | 5 |
| 80 | 20 | 1000 | 1 | 50 | 5 |
| 80 | 20 | 1000 | 7 | 50 | 5 |
| 80 | 20 | 1000 | 15 | 50 | 5 |
| 80 | 20 | 1000 | 30 | 50 | 5 |
| 60 | 40 | 1000 | 50 | 50 | 5 |
| 80 | 20 | 1000 | 10 | 0.1 | 5 |
| 80 | 20 | 1000 | 10 | 50 | 5 |
| 80 | 20 | 1000 | 10 | 200 | 5 |
| 80 | 20 | 1000 | 10 | 750 | 5 |
| 80 | 20 | 1000 | 10 | 1,500 | 5 |
| 80 | 20 | 1000 | 10 | 5,000 | 5 |

TABLE 2-continued

Formulations of electrochemical deblocking solutions.

| Solvent | Alcohol | Acid Source | Reducible Chemical | Organic Salt | Organic Base |
|---|---|---|---|---|---|
| 80 | 20 | 1000 | 10 | 100 | 0.01 |
| 80 | 20 | 1000 | 10 | 100 | 2 |
| 80 | 20 | 1000 | 10 | 100 | 7 |
| 80 | 20 | 1000 | 10 | 100 | 20 |
| 80 | 20 | 1000 | 10 | 100 | 75 |
| 80 | 20 | 1000 | 10 | 100 | 200 |
| 100 | 0 | 750 | 10 | 50 | 10 |
| 80 | 20 | 1000 | 10 | 50 | 10 |
| 60 | 40 | 1000 | 10 | 50 | 10 |
| 40 | 60 | 1000 | 10 | 50 | 10 |
| 20 | 80 | 1000 | 10 | 50 | 10 |
| 0 | 100 | 1000 | 10 | 50 | 10 |
| 80 | 20 | 0.1 | 10 | 50 | 10 |
| 80 | 20 | 50 | 10 | 50 | 10 |
| 80 | 20 | 200 | 10 | 50 | 10 |
| 80 | 20 | 1000 | 10 | 50 | 10 |
| 80 | 20 | 2000 | 10 | 50 | 10 |
| 60 | 40 | 2000 | 10 | 50 | 10 |
| 80 | 20 | 1000 | 0.1 | 50 | 10 |
| 80 | 20 | 1000 | 1 | 50 | 10 |
| 80 | 20 | 1000 | 7 | 50 | 10 |
| 80 | 20 | 1000 | 15 | 50 | 10 |
| 80 | 20 | 1000 | 30 | 50 | 10 |
| 60 | 40 | 1000 | 50 | 50 | 10 |
| 80 | 20 | 1000 | 10 | 0.1 | 10 |
| 80 | 20 | 1000 | 10 | 50 | 10 |
| 80 | 20 | 1000 | 10 | 200 | 10 |
| 80 | 20 | 1000 | 10 | 750 | 10 |
| 80 | 20 | 1000 | 10 | 1,500 | 10 |
| 80 | 20 | 1000 | 10 | 5,000 | 10 |
| 80 | 20 | 2000 | 10 | 100 | 0.01 |
| 80 | 20 | 2000 | 10 | 100 | 2 |
| 80 | 20 | 2000 | 10 | 100 | 7 |
| 80 | 20 | 2000 | 10 | 100 | 20 |
| 80 | 20 | 2000 | 10 | 100 | 75 |
| 80 | 20 | 2000 | 10 | 100 | 200 |
| 100 | 0 | 750 | 10 | 50 | 5 |
| 80 | 20 | 1000 | 10 | 50 | 5 |
| 60 | 40 | 1000 | 10 | 50 | 5 |
| 40 | 60 | 1000 | 10 | 50 | 5 |
| 20 | 80 | 1000 | 10 | 50 | 5 |
| 0 | 100 | 1000 | 10 | 50 | 5 |
| 90 | 10 | 0.1 | 10 | 50 | 5 |
| 90 | 10 | 50 | 10 | 50 | 5 |
| 90 | 10 | 200 | 10 | 50 | 5 |
| 90 | 10 | 1000 | 10 | 50 | 5 |
| 90 | 10 | 2000 | 10 | 50 | 5 |
| 60 | 40 | 2000 | 10 | 50 | 5 |
| 90 | 10 | 1000 | 0.1 | 50 | 5 |
| 90 | 10 | 1000 | 1 | 50 | 5 |
| 90 | 10 | 1000 | 7 | 50 | 5 |
| 90 | 10 | 1000 | 15 | 50 | 5 |
| 90 | 10 | 1000 | 30 | 50 | 5 |
| 90 | 10 | 1000 | 50 | 50 | 5 |
| 90 | 10 | 1000 | 10 | 0.1 | 5 |
| 90 | 10 | 1000 | 10 | 50 | 5 |
| 90 | 10 | 1000 | 10 | 200 | 5 |
| 90 | 10 | 1000 | 10 | 750 | 5 |
| 90 | 10 | 1000 | 10 | 1,500 | 5 |
| 90 | 10 | 1000 | 10 | 5,000 | 5 |
| 90 | 10 | 1000 | 10 | 100 | 0.01 |
| 90 | 10 | 1000 | 10 | 100 | 2 |
| 90 | 10 | 1000 | 10 | 100 | 7 |
| 90 | 10 | 1000 | 10 | 100 | 20 |
| 90 | 10 | 1000 | 10 | 100 | 75 |
| 90 | 10 | 1000 | 10 | 100 | 200 |

| Acetonitrile (%) | Methanol (%) | Hydroquinone (mM) | Anthraquinone (mM) | Tetraethyl ammonium p-toluene sulfonate (mM) | Lutidine (mM) |
|---|---|---|---|---|---|
| 100 | 0 | 50 | 2.5 | 50 | 5 |
| 80 | 20 | 50 | 2.5 | 50 | 5 |

TABLE 2-continued

Formulations of electrochemical deblocking solutions.

| Solvent | Alcohol | Acid Source | Reducible Chemical | Organic Salt | Organic Base |
|---|---|---|---|---|---|
| 60 | 40 | 50 | 2.5 | 50 | 5 |
| 40 | 60 | 50 | 2.5 | 50 | 5 |
| 20 | 80 | 50 | 2.5 | 50 | 5 |
| 0 | 100 | 50 | 2.5 | 50 | 5 |
| 90 | 10 | 0.1 | 2.5 | 50 | 5 |
| 90 | 10 | 1 | 2.5 | 50 | 5 |
| 90 | 10 | 5 | 2.5 | 50 | 5 |
| 90 | 10 | 10 | 2.5 | 50 | 5 |
| 90 | 10 | 30 | 2.5 | 50 | 5 |
| 60 | 40 | 40 | 2.5 | 50 | 5 |
| 90 | 10 | 50 | 0.01 | 50 | 5 |
| 90 | 10 | 50 | .1 | 50 | 5 |
| 90 | 10 | 50 | .5 | 50 | 5 |
| 90 | 10 | 50 | 1 | 50 | 5 |
| 90 | 10 | 50 | 1.5 | 50 | 5 |
| 90 | 10 | 50 | 2 | 50 | 5 |
| 90 | 10 | 50 | 2.5 | 0.1 | 5 |
| 90 | 10 | 50 | 2.5 | 50 | 5 |
| 90 | 10 | 50 | 2.5 | 200 | 5 |
| 90 | 10 | 50 | 2.5 | 750 | 5 |
| 90 | 10 | 50 | 2.5 | 1,500 | 5 |
| 90 | 10 | 50 | 2.5 | 5,000 | 5 |
| 90 | 10 | 50 | 2.5 | 100 | 0.01 |
| 90 | 10 | 50 | 2.5 | 100 | 2 |
| 90 | 10 | 50 | 2.5 | 100 | 7 |
| 90 | 10 | 50 | 2.5 | 100 | 20 |
| 90 | 10 | 50 | 2.5 | 100 | 75 |
| 90 | 10 | 50 | 2.5 | 100 | 200 |

| Acetonitrile (%) | Methanol (%) | Hydroquinone (mM) | Benzoquinone (mM) | Tetraethyl ammonium p-toluene sulfonate (mM) | Lutidine (mM) |
|---|---|---|---|---|---|
| 100 | 0 | 500 | 10 | 50 | 5 |
| 80 | 20 | 500 | 10 | 50 | 5 |
| 60 | 40 | 500 | 10 | 50 | 5 |
| 40 | 60 | 500 | 10 | 50 | 5 |
| 20 | 80 | 500 | 10 | 50 | 5 |
| 0 | 100 | 500 | 10 | 50 | 5 |
| 100 | 0 | 0.1 | 10 | 50 | 5 |
| 100 | 0 | 1 | 10 | 50 | 5 |
| 100 | 0 | 10 | 10 | 50 | 5 |
| 100 | 0 | 100 | 10 | 50 | 5 |
| 100 | 0 | 400 | 10 | 50 | 5 |
| 100 | 0 | 750 | 10 | 50 | 5 |
| 100 | 0 | 500 | 0.1 | 50 | 5 |
| 100 | 0 | 500 | 1 | 50 | 5 |
| 100 | 0 | 500 | 7 | 50 | 5 |
| 100 | 0 | 500 | 15 | 50 | 5 |
| 100 | 0 | 500 | 30 | 50 | 5 |
| 100 | 0 | 500 | 50 | 50 | 5 |
| 100 | 0 | 500 | 10 | 0.1 | 5 |
| 100 | 0 | 500 | 10 | 50 | 5 |
| 100 | 0 | 500 | 10 | 200 | 5 |
| 100 | 0 | 500 | 10 | 750 | 5 |
| 100 | 0 | 500 | 10 | 1,500 | 5 |
| 100 | 0 | 500 | 10 | 5,000 | 5 |
| 100 | 0 | 500 | 10 | 100 | 0.0001 |
| 100 | 0 | 500 | 10 | 100 | .001 |
| 100 | 0 | 500 | 10 | 100 | .01 |
| 100 | 0 | 500 | 10 | 100 | .1 |
| 100 | 0 | 500 | 10 | 100 | 10 |
| 100 | 0 | 500 | 10 | 100 | 200 |

| Methylene Chloride (%) | Methanol (%) | Hydroquinone (mM) | Benzoquinone (mM) | Tetraethyl ammonium p-toluene sulfonate (mM) | Lutidine (mM) |
|---|---|---|---|---|---|
| 100 | 0 | 750 | 10 | 50 | 5 |
| 80 | 20 | 1000 | 10 | 50 | 5 |
| 60 | 40 | 1000 | 10 | 50 | 5 |

TABLE 2-continued

Formulations of electrochemical deblocking solutions.

| Solvent | Alcohol | Acid Source | Reducible Chemical | Organic Salt | Organic Base |
|---|---|---|---|---|---|
| 40 | 60 | 1000 | 10 | 50 | 5 |
| 20 | 80 | 1000 | 10 | 50 | 5 |
| 0 | 100 | 1000 | 10 | 50 | 5 |
| 80 | 20 | 0.1 | 10 | 50 | 5 |
| 80 | 20 | 50 | 10 | 50 | 5 |
| 80 | 20 | 200 | 10 | 50 | 5 |
| 80 | 20 | 1000 | 10 | 50 | 5 |
| 80 | 20 | 2,000 | 10 | 50 | 5 |
| 60 | 40 | 2,000 | 10 | 50 | 5 |
| 80 | 20 | 1000 | 0.1 | 50 | 5 |
| 80 | 20 | 1000 | 1 | 50 | 5 |
| 80 | 20 | 1000 | 7 | 50 | 5 |
| 80 | 20 | 1000 | 15 | 50 | 5 |
| 80 | 20 | 1000 | 30 | 50 | 5 |
| 60 | 40 | 1000 | 50 | 50 | 5 |
| 80 | 20 | 1000 | 10 | 0.1 | 5 |
| 80 | 20 | 1000 | 10 | 50 | 5 |
| 80 | 20 | 1000 | 10 | 200 | 5 |
| 80 | 20 | 1000 | 10 | 750 | 5 |
| 80 | 20 | 1000 | 10 | 1,500 | 5 |
| 80 | 20 | 1000 | 10 | 5,000 | 5 |
| 80 | 20 | 1000 | 10 | 100 | 0.01 |
| 80 | 20 | 1000 | 10 | 100 | 2 |
| 80 | 20 | 1000 | 10 | 100 | 7 |
| 80 | 20 | 1000 | 10 | 100 | 20 |
| 80 | 20 | 1000 | 10 | 100 | 75 |
| 80 | 20 | 1000 | 10 | 100 | 200 |

| Dichloromethane (%) | Isopropanol (%) | 2,5-di tert-butyl hydroquinone (mM) | 2,5-di tert-butyl benzoquinone (mM) | Tetrabutyl ammonium hexafluoro phosphate (mM) | N,N-diisopropyl ethyl amine (mM) |
|---|---|---|---|---|---|
| 100 | 0 | 10 | 10 | 50 | 10 |
| 80 | 20 | 10 | 10 | 50 | 10 |
| 60 | 40 | 10 | 10 | 50 | 10 |
| 40 | 60 | 10 | 10 | 50 | 10 |
| 20 | 80 | 10 | 10 | 50 | 10 |
| 0 | 100 | 10 | 10 | 50 | 10 |
| 90 | 10 | 0.1 | 10 | 50 | 10 |
| 90 | 10 | 1 | 10 | 50 | 10 |
| 90 | 10 | 25 | 10 | 50 | 10 |
| 90 | 10 | 50 | 10 | 50 | 10 |
| 90 | 10 | 75 | 10 | 50 | 10 |
| 90 | 10 | 100 | 10 | 50 | 10 |
| 90 | 10 | 10 | 0.1 | 50 | 10 |
| 90 | 10 | 10 | 50 | 50 | 10 |
| 90 | 10 | 10 | 75 | 50 | 10 |
| 90 | 10 | 10 | 125 | 50 | 10 |
| 90 | 10 | 10 | 175 | 50 | 10 |
| 90 | 10 | 10 | 200 | 50 | 10 |
| 90 | 10 | 10 | 10 | 0.1 | 10 |
| 90 | 10 | 10 | 10 | 50 | 10 |
| 90 | 10 | 10 | 10 | 200 | 10 |
| 90 | 10 | 10 | 10 | 300 | 10 |
| 90 | 10 | 10 | 10 | 500 | 10 |
| 90 | 10 | 10 | 10 | 750 | 10 |
| 90 | 10 | 10 | 10 | 100 | 0.01 |
| 90 | 10 | 10 | 10 | 100 | 2 |
| 90 | 10 | 10 | 10 | 100 | 7 |
| 90 | 10 | 10 | 10 | 100 | 20 |
| 90 | 10 | 38 | 10 | 100 | 75 |
| 90 | 10 | 100 | 10 | 100 | 200 |

| Dichloromethane (%) | Isopropanol (%) | 2,5-di tert-butyl hydroquinone (mM) | Anthraquinone (mM) | Tetraethyl ammonium p-toluene sulfonate (mM) | N,N-diisopropyl ethyl amine (mM) |
|---|---|---|---|---|---|
| 100 | 0 | 10 | 1 | 50 | 10 |
| 80 | 20 | 10 | 1 | 50 | 10 |
| 60 | 40 | 10 | 1 | 50 | 10 |
| 40 | 60 | 10 | 1 | 50 | 10 |

TABLE 2-continued

Formulations of electrochemical deblocking solutions.

| Solvent | Alcohol | Acid Source | Reducible Chemical | Organic Salt | Organic Base |
|---|---|---|---|---|---|
| 20 | 80 | 10 | 1 | 50 | 10 |
| 0 | 100 | 10 | 1 | 50 | 10 |
| 80 | 20 | 0.1 | 0.001 | 50 | 10 |
| 80 | 20 | 1 | .05 | 50 | 10 |
| 80 | 20 | 25 | .5 | 50 | 10 |
| 80 | 20 | 50 | 1.2 | 50 | 10 |
| 80 | 20 | 75 | 3 | 50 | 10 |
| 80 | 20 | 100 | 5 | 50 | 10 |
| 80 | 20 | 10 | 1 | 50 | 10 |
| 80 | 20 | 10 | 1 | 50 | 10 |
| 80 | 20 | 10 | 1 | 50 | 10 |
| 80 | 20 | 10 | 1 | 50 | 10 |
| 80 | 20 | 10 | 1 | 50 | 10 |
| 80 | 20 | 10 | 1 | 50 | 10 |
| 80 | 20 | 10 | 1 | 0.1 | 10 |
| 80 | 20 | 10 | 1 | 50 | 10 |
| 80 | 20 | 10 | 1 | 200 | 10 |
| 80 | 20 | 10 | 1 | 300 | 10 |
| 80 | 20 | 10 | 1 | 500 | 10 |
| 80 | 20 | 10 | 1 | 750 | 10 |
| 80 | 20 | 10 | 1 | 100 | 0.01 |
| 80 | 20 | 10 | 1 | 100 | 2 |
| 80 | 20 | 10 | 1 | 100 | 7 |
| 80 | 20 | 10 | 1 | 100 | 20 |
| 80 | 20 | 38 | 1 | 100 | 75 |
| 80 | 20 | 100 | 1 | 100 | 200 |

| Dichloro-methane (%) | Isopropanol (%) | 2,5-di tert-butyl hydroquinone (mM) | 2,6-Dimethoxy benzoquinone (mM) | Tetraethyl ammonium p-toluene sulfonate (mM) | N,N-diisopropyl ethyl amine (mM) |
|---|---|---|---|---|---|
| 100 | 0 | 10 | 10 | 50 | 10 |
| 80 | 20 | 10 | 10 | 50 | 10 |
| 60 | 40 | 10 | 10 | 50 | 10 |
| 40 | 60 | 10 | 10 | 50 | 10 |
| 20 | 80 | 10 | 10 | 50 | 10 |
| 0 | 100 | 10 | 10 | 50 | 10 |
| 80 | 20 | 0.1 | 10 | 50 | 10 |
| 80 | 20 | 1 | 10 | 50 | 10 |
| 80 | 20 | 25 | 10 | 50 | 10 |
| 80 | 20 | 50 | 10 | 50 | 10 |
| 80 | 20 | 75 | 10 | 50 | 10 |
| 80 | 20 | 100 | 10 | 50 | 10 |
| 80 | 20 | 10 | 0.1 | 50 | 10 |
| 80 | 20 | 10 | 50 | 50 | 10 |
| 80 | 20 | 10 | 75 | 50 | 10 |
| 80 | 20 | 10 | 125 | 50 | 10 |
| 80 | 20 | 10 | 175 | 50 | 10 |
| 80 | 20 | 10 | 200 | 50 | 10 |
| 80 | 20 | 10 | 10 | 0.1 | 10 |
| 80 | 20 | 10 | 10 | 50 | 10 |
| 80 | 20 | 10 | 10 | 200 | 10 |
| 80 | 20 | 10 | 10 | 750 | 10 |
| 80 | 20 | 10 | 10 | 1,500 | 10 |
| 80 | 20 | 10 | 10 | 5,000 | 10 |
| 80 | 20 | 10 | 10 | 100 | 0.01 |
| 80 | 20 | 10 | 10 | 100 | 2 |
| 80 | 20 | 10 | 10 | 100 | 7 |
| 80 | 20 | 10 | 10 | 100 | 20 |
| 80 | 20 | 38 | 10 | 100 | 75 |
| 80 | 20 | 100 | 10 | 100 | 200 |

| Diemthyl sulfoxide (%) | Isoamyl alcohol (%) | Thiophenol (mM) | 2,3-Dimethyl naphtha quinone (mM) | bis(pentafluoro ethyl) phosphinate (mM) | Pyrazole (mM) |
|---|---|---|---|---|---|
| 100 | 0 | 10 | 10 | 50 | 10 |
| 80 | 20 | 10 | 10 | 50 | 10 |
| 60 | 40 | 10 | 10 | 50 | 10 |
| 40 | 60 | 10 | 10 | 50 | 10 |
| 20 | 80 | 10 | 10 | 50 | 10 |
| 0 | 100 | 10 | 10 | 50 | 10 |

TABLE 2-continued

Formulations of electrochemical deblocking solutions.

| Solvent | Alcohol | Acid Source | Reducible Chemical | Organic Salt | Organic Base |
|---|---|---|---|---|---|
| 80 | 20 | 0.1 | 10 | 50 | 10 |
| 80 | 20 | 1 | 10 | 50 | 10 |
| 80 | 20 | 25 | 10 | 50 | 10 |
| 80 | 20 | 50 | 10 | 50 | 10 |
| 80 | 20 | 75 | 10 | 50 | 10 |
| 80 | 20 | 100 | 10 | 50 | 10 |
| 80 | 20 | 10 | 0.1 | 50 | 10 |
| 80 | 20 | 10 | 50 | 50 | 10 |
| 80 | 20 | 10 | 75 | 50 | 10 |
| 80 | 20 | 10 | 125 | 50 | 10 |
| 80 | 20 | 10 | 175 | 50 | 10 |
| 80 | 20 | 10 | 200 | 50 | 10 |
| 80 | 20 | 10 | 10 | 0.1 | 10 |
| 80 | 20 | 10 | 10 | 50 | 10 |
| 80 | 20 | 10 | 10 | 75 | 10 |
| 80 | 20 | 10 | 10 | 125 | 10 |
| 80 | 20 | 10 | 10 | 175 | 10 |
| 80 | 20 | 10 | 10 | 200 | 10 |
| 80 | 20 | 10 | 10 | 100 | 0.01 |
| 80 | 20 | 10 | 10 | 100 | 2 |
| 80 | 20 | 10 | 10 | 100 | 7 |
| 80 | 20 | 10 | 10 | 100 | 20 |
| 80 | 20 | 38 | 10 | 100 | 75 |
| 80 | 20 | 100 | 10 | 100 | 200 |

What is claimed is:

1. An electrochemical deblocking solution comprising:
   an organic base including N,N-diisopropylethylamine, a benzoquinone and a hydroquinone;
   tetrabutylammonium hexafluorophosphate as an organic salt; and
   a solvent including acetonitrile and an alcohol.

2. The electrochemical deblocking solution of claim 1, where the solvent has approximately 1% to 99% acetonitrile and approximately 1% to 99% isopropanol.

3. The electrochemical deblocking solution of claim 1, where the N,N-diisopropylethylamine is approximately 0.01 to 200 mM of N,N-diisopropylethylamine.

4. The electrochemical deblocking solution of claim 1, where the benzoquinone is approximately 0.1 to 100 mM 2,5-di-tert-butyl benzoquinone.

5. The electrochemical deblocking solution of claim 1, where the hydroquinone is approximately 0.1 to 100 mM 2,5-di-tert-butyl hydroquinone.

6. The electrochemical deblocking solution of claim 1, where the tetrabutylammonium hexafluorophosphate is approximately 0.05 to 5 M tetrabutylammonium hexafluorophosphate.

7. The electrochemical deblocking solution of claim 6, where the N,N-diisopropylethylamine is approximately 0.01 to 200 mM of N,N-diisopropylethylamine, the hydroquinone is approximately 0.1 to 100 mM 2,5-di-tert-butyl hydroquinone and the benzoquinone is approximately 0.1 to 100 mM 2,5-di-tert-butyl benzoquinone.

8. An electrochemical deblocking solution comprising:
   an organic base including a lutidine, a benzoquinone and a hydroquinone;
   tetraethylammonium p-toluenesulfonate as an organic salt; and
   a solvent selected from the group consisting of two or more of an alcohol, acetonitrile and dichloromethane.

9. The electrochemical deblocking solution of claim 8 for use on a prepared surface, where the lutidine is not bound to the prepared surface.

10. The electrochemical deblocking solution of claim 8, where the solvent has approximately 10% to 99% acetonitrile and approximately 1% to 90% methanol.

11. The electrochemical deblocking solution of claim 8, where the solvent has approximately 1% to 99% dichloromethane and approximately 1% to 99% isopropanol.

12. The electrochemical deblocking solution of claim 8, where the lutidine is approximately 0.01 to 200 mM of dimethyl pyridine.

13. The electrochemical deblocking solution of claim 8, where the benzoquinone is approximately 0.1 to 100 mM 2,5-di-tert-butyl benzoquinone.

14. The electrochemical deblocking solution of claim 8, where the hydroquinone is approximately 0.1 to 100 mM 2,5-di-tert-butyl hydroquinone.

15. The electrochemical deblocking solution of claim 8, where the tetraethylammonium p-toluenesulfonate is approximately 0.1 mM to 5 M tetraethylammonium p-toluenesulfonate.

16. The electrochemical deblocking solution of claim 15, where the lutidine is approximately 0.01 to 200 mM of dimethyl pyridine, the hydroquinone is approximately 0.1 to 100 mM 2,5-di-tert-butyl hydroquinone and the benzoquinone is approximately 0.1 to 100 mM 2,5-di-tert-butyl benzoquinone.

17. The electrochemical deblocking solution of claim 10, where the tetraethylammonium p-toluenesulfonate is dissolved in the acetonitrile and methanol solvent to form a first solution and the lutidine provides basicity to quench the acidity of the tetraethylammonium p-toluenesulfonate in acetonitrile and methanol solution.

18. The electrochemical deblocking solution of claim 11, where the tetraethylammonium p-toluenesulfonate is dissolved in the dichloromethane and isopropanol solvent to form a first solution and the lutidine provides basicity to quench the acidity of the tetraethylammonium p-toluenesulfonate in dichloromethane and isopropanol solution.

19. An electrochemical deblocking solution for use on an electrode microarray comprising:
   approximately 0.01 to 200 mM of a pyridine derivative or isomer thereof, where the pyridine derivative or isomer thereof is not bound to the electrode microarray;
   approximately 0.1 to 100 mM 2,5-di-tert-butyl benzoquinone;
   approximately 0.1 to 100 mM 2,5-di-tert-butyl hydroquinone;
   approximately 0.1 mM to 5 M tetraethylammonium p-toluenesulfonate; and
   a solvent having approximately 10% to 99% acetonitrile and approximately 1% to 90% methanol.

20. The electrochemical deblocking solution of claim 19, where the pyridine derivative or isomer thereof is selected from the group consisting of

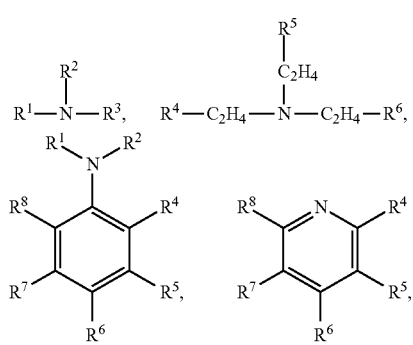

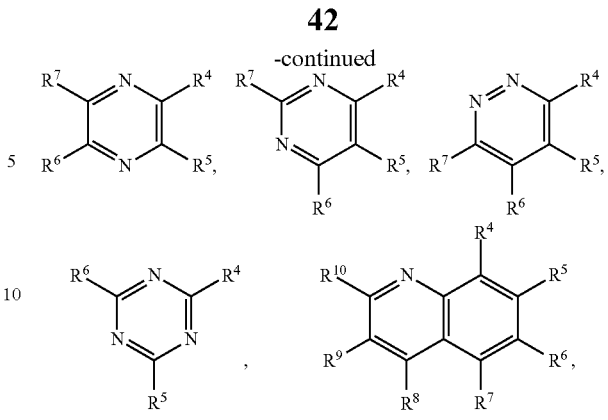

where $R^1$, $R^2$, and $R^3$ are independently selected from the group consisting of hydrogen, and substituted and unsubstituted alkyl, alkenyl, alkynyl, cycloalkyl, cycloalkenyl, cycloalkynyl, aryl, heterocyclic ring, and polycyclic group, and halo, amide, carboxy, amino, secondary amino, tertiary amino, hydrazino, azido, alkazoxy, cyano, isocyano, cyanato, thiocyanato, fulminato, selenocyanato, carboxyamido, acylimino, nitroso, aminooxy, hydrazonoyl, oxime, acylhydrazino, amidino, sulfide, thiosulfoxide, sulfone, thiosulfone, thiosulfate, hydroxyl, formyl, hydroperoxy, carbamoyl, trimethyl silyl, nitro, nitroso, oxamoyl, pentazolyl, sulfamoyl, sulfenamoyl, sulfeno, sulfinamoyl, sulfino, sulfo, sulfoamino, hydrothiol, tetrazolyl, thiocarbamoyl, thiocarbazono, thiocarbodiazono, thiocarbonohydrazido, thiocarboxy, thioformyl, thioacyl, thiocyanato, thiosemicarbazido, thiosulfino, thiosulfo, thioureido, triazano, triazeno, triazinyl, trithiosulfo, and phosphoric acid ester; $R^4$ and $R^8$ are independently selected from the group consisting of hydrogen, and substituted and unsubstituted alkyl $C_2$ to alkyl $C_8$, alkenyl, alkynyl, cycloalkyl, cycloalkenyl, cycloalkynyl, aryl, heterocyclic ring, and polycyclic group, and halo, amide, alkoxy, acyl, acyloxy, oxycarbonyl, alkoxycarbonyloxy, carboxy, amino, secondary amino, tertiary amino, hydrazino, azido, alkazoxy, cyano, isocyano, cyanato, thiocyanato, fulminato, selenocyanato, carboxyamido, acylimino, nitroso, aminooxy, carboximidoyl, hydrazonoyl, oxime, acylhydrazino, amidino, sulfide, sulfoxide, thiosulfoxide, sulfone, thiosulfone, thiosulfate, hydroxyl, formyl, hydroxyperoxy, hydroperoxy, peroxy acid, carbamoyl, trimethyl silyl, nitro, nitroso, oxamoyl, pentazolyl, sulfamoyl, sulfenamoyl, sulfeno, sulfinamoyl, sulfino, sulfo, sulfoamino, hydrothiol, tetrazolyl, thiocarbamoyl, thiocarbazono, thiocarbodiazono, thiocarbonohydrazido, thiocarboxy, thioformyl, thioacyl, thiocyanato, thiosemicarbazido, thiosulfino, thiosulfo, thioureido, triazano, triazeno, triazinyl, trithiosulfo, and phosphoric acid ester; and $R^5$, $R^6$, $R^7$, $R^9$, and $R^{10}$ are independently selected from the group consisting of hydrogen, and substituted and unsubstituted alkyl, alkenyl, alkynyl, cycloalkyl, cycloalkenyl, cycloalkynyl, aryl, heterocyclic ring, and polycyclic group, and halo, amide, alkoxy, acyl, acyloxy, oxycarbonyl, alkoxycarbonyloxy, carboxy, amino, secondary amino, tertiary amino, hydrazino, azido, alkazoxy, cyano, isocyano, cyanato, thiocyanato, fulminato, selenocyanato, carboxyamido, acylimino, nitroso, aminooxy, carboximidoyl, hydrazonoyl, oxime, acylhydrazino, amidino, sulfide, sulfoxide, thiosulfoxide, sulfone, thiosulfone, thiosulfate, hydroxyl, formyl, hydroxyperoxy, hydroperoxy, peroxy acid, carbamoyl, trimethyl silyl, nitro, nitroso, oxamoyl, pentazolyl, sulfamoyl, sulfenamoyl, sulfeno, sulfinamoyl, sulfino, sulfo, sulfoamino, hydrothiol, tetrazolyl, thiocarbamoyl, thiocarbazono, thiocarbodiazono, thiocarbonohydrazido, thiocarboxy, thioformyl, thioacyl, thiocyanato, thiosemicarbazido, thiosulfino, thiosulfo, thioureido, triazano, triazeno, triazinyl, trithiosulfo, and phosphoric acid ester.

* * * * *